United States Patent [19]

Müller et al.

[11] 4,234,578

[45] Nov. 18, 1980

[54] AMINOETHYL-METHOXY-CEPHALOSPORIN COMPOUNDS

[75] Inventors: Beat Müller, Reinach; Peter Schneider, Basel; Heinrich Peter; Hans Bickel, both of Binningen, all of Switzerland

[73] Assignee: Ciba-Geigy Corporation, Ardsley, N.Y.

[21] Appl. No.: 912,822

[22] Filed: Jun. 5, 1978

Related U.S. Application Data

[63] Continuation of Ser. No. 592,497, Jul. 2, 1975, abandoned, which is a continuation-in-part of Ser. No. 505,887, Sep. 13, 1974, abandoned.

[30] Foreign Application Priority Data

| Oct. 1, 1973 | [CH] | Switzerland | 14034/73 |
| Jan. 21, 1974 | [CH] | Switzerland | 785/74 |
| Jul. 12, 1974 | [CH] | Switzerland | 9640/74 |
| Jul. 12, 1974 | [CH] | Switzerland | 9641/74 |
| Feb. 7, 1975 | [CH] | Switzerland | 1551/75 |

[51] Int. Cl.$^3$ .......................................... C07D 501/57
[52] U.S. Cl. ...................................... 424/246; 544/21
[58] Field of Search ........................ 544/21; 424/246

[56] References Cited

U.S. PATENT DOCUMENTS 4,024,249  5/1977  Müller et al. .......................... 544/27

Primary Examiner—Nicholas S. Rizzo
Attorney, Agent, or Firm—John J. Maitner

[57] ABSTRACT

6$\beta$-($R_a$)($R_b$)N-methylaryl-acetylamino-6$\alpha$-methoxy-2,2-dimethylpenam-3-carboxylic acid compounds and 7$\beta$-($R_a$)($R_b$)N-methylaryl-acetylamino-7$\alpha$-methoxy-3-cephem-4-carboxylic acid compounds, wherein $R_a$ and $R_b$ independently of each other represent hydrogen or optionally substituted lower alkyl, or wherein $R_a$ and $R_b$ conjointly denote optionally substituted lower alkylene, wherein the aminomethyl-substituted aryl radical represents a corresponding thienyl, furyl or phenyl radical, and wherein the 3-position in 3-cephem compounds is unsubstituted or substituted by a modified hydroxyl group or an optionally substituted methyl group, exhibit antibiotic action against Gram-negative or Gram-positive micro-organisms.

16 Claims, No Drawings

AMINOETHYL-METHOXY-CEPHALOSPORIN COMPOUNDS

This is a continuation of application Ser. No. 592,497, filed on July 2, 1975 now abandoned which in turn is a continuation-in-part of application Ser. No. 505,887, filed Sept. 13, 1974, now abandoned.

The present invention relates to N-substituted aminomethyl-methoxy-heterocyclic compounds, especially 6β-acylamino-6α-methoxy-penam-3-carboxylic acid compounds and 7β-acylamino-7-methoxy-3-cephem-4-carboxylic acid compounds of the formula

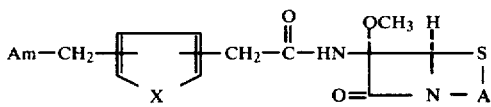

wherein Am represents an amino group of the formula

in which $R_a$ and $R_b$ independently of each other represent hydrogen or optionally substituted lower alkyl, or in which $R_a$ and $R_b$ conjointly denote optionally substituted lower alkylene, and X represents sulphur or oxygen or represents ethenylene of the formula —CH=CH—, and wherein the grouping of the formula —S—A— denotes a radical of the formula

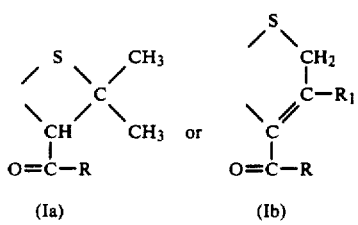

in which $R_1$ represents hydrogen, an etherified hydroxyl group or a radical of the formula —CH$_2$—R$_2$—, wherein $R_2$ denotes hydrogen, a free, etherified or esterfied hydroxyl or mercapto group or a quaternary ammonium group, and R represents hydroxyl or an etherified hydroxyl group which, together with the carbonyl grouping —C(=O)—, forms an esterified carboxyl group which can be split under physiological conditions, as well as salts thereof and also processes for their manufacture as well as pharmaceutical preparations containing such compounds, and the use of such pharmaceutical preparations.

Lower alkyl $R_a$ and/or $R_b$ contains preferably up to 7, especially up to 4, carbon atoms and above all represents methyl, as well as ethyl, n-propyl, isopropyl, n-butyl, isobutyl, sec.-butyl, tert.-butyl, n-pentyl, n-hexyl, isohexyl or n-heptyl. Substituents are in particular optionally functionally modified, such as optionally etherified or esterified, hydroxyl, for example lower alkoxy, such as methoxy, ethoxy, n-propoxy, isopropoxy or isobutoxy, or halogen, such as chlorine or bromine, optionally functionally modified hydroxyl preferably being separated from the nitrogen atom of the amino group by at least two carbon atoms of a lower alkyl radical $R_a$ and/or $R_b$), or optionally functionally modified carboxyl, such as esterified or amidised carboxyl, for example lower alkoxycarbonyl, such as methoxycarbonyl or ethoxycarbonyl, or carbamoyl, as well as cyano.

A lower alkylene formed by $R_a$ and $R_b$ conjointly is, for example, 1,2-ethylene, 1,3-propylene and, above all, 1,4-butylene or 1,5-pentylene, as well as 3-methyl-1,5-pentylene or 1,6-hexylene. Substituents of such lower alkylene radicals are, for example, the abovementioned optionally functionally modified hydroxyl and/or carboxyl groups.

The group X is above all sulphur but can also be oxygen as well as ethylene of the formula —CH=CH—. The Am-methyl-substituted radical thus represents the corresponding Am-methyl-thienyl, for example 4- or 5-Am-methyl-2- or -3-thienyl, also 3-Am-methyl-2-thienyl or 2-Am-methyl-3-thienyl, or corresponding Am-methyl-furyl, for example 4- or 5-Am-methyl-2-furyl, as well as corresponding Am-methyl-phenyl, for example 2- or 4-Am-methyl-phenyl.

An etherified hydroxyl group $R_1$ is a hydroxyl group etherified by a lower aliphatic hydrocarbon radical. Such a group is, in particular, lower alkoxy, preferably with up to 7, especially with up to 4, carbon atoms, above all methoxy, as well as ethoxy, n-propoxy or isopropoxy and also straight-chain or branched butoxy, pentoxy, hexyloxy or heptyloxy.

An etherified hydroxyl or mercapto group $R_2$ is, for example, a hydroxyl or mercapto group etherified by a lower aliphatic hydrocarbon radical. An etherified mercapto group $R_2$ can also represent a mercapto group etherified by an optionally substituted heterocyclic radical which is bonded to the sulphur via a ring carbon atom and which has 1 to 4 ring nitrogen atoms and optionally a further ring hetero-atom from the group oxygen and sulphur.

An esterified hydroxyl or mercapto group $R_2$ is a hydroxyl or mercapto group esterified by a lower aliphatic carboxylic acid or by an optionally N-substituted carbamic acid. A mercapto group can also be esterified by benzoic acid or by a heterocyclic carboxylic acid, wherein the heterocyclic part represents an optionally substituted heterocyclic radical which is bonded to the sulphur via a ring carbon atom and which has 1 to 4 ring nitrogen atoms and optionally a further ring hetero-atom from the group oxygen and sulphur.

Quaternary ammonium groups $R_2$ are quaternary ammonium groups which are derived from tertiary organic bases, preferably from corresponding aliphatic amines or above all from corresponding heterocyclic nitrogen bases, and which are bonded to the methyl carbon atom via the nitrogen atom.

Hydroxyl and mercapto groups $R_2$ etherified with an aliphatic hydrocarbon radical are, in particular, lower alkoxy, preferably with up to 7, especially up to 4, carbon atoms, above all methoxy as well as ethoxy, n-propoxy or isopropoxy and also straight-chain or branched butoxy, pentoxy, hexyloxy or heptyloxy, or lower alkylthio, preferably with up to 7, especially with up to 4, carbon atoms, above all methylthio as well as ethylthio, n-propylthio or isopropylthio and also straight-chain or branched butylthio, pentylthio, hexylthio or heptylthio.

In a mercapto group $R_2$ etherified by the heterocyclic radical mentioned, this radical has aromatic properties or can be partially saturated. Substituents are, inter alia, lower alkyl, especially methyl, as well as ethyl, n-propyl, isopropyl or straight-chain or branched butyl, pentyl or hexyl, hydroxy-lower alkyl, for example hydroxymethyl, cycloalkyl, for example cyclopentyl or cyclohexyl, aryl, such as phenyl which is optionally substituted by halogen, for example chlorine, or by nitro, aryl-lower alkyl, for example benzyl, or heterocyclyl, such as furyl, for example 2-furyl, thienyl, for example 2-thienyl, or oxazolyl, for example 2-oxazolyl, or functional groups, such as halogen, for example fluorine, chlorine or bromine, optionally substituted amino, such as amino which is optionally monosubstituted or disubstituted by lower alkyl, for example amino, methylamino or dimethylamino, nitro, hydroxyl, lower alkoxy, for example methoxy, ethoxy, n-butoxy or 2-ethylhexyloxy, or optionally functionally modified carboxyl, such as carboxyl, esterified carboxyl, such as lower alkoxycarbonyl, for example methoxycarbonyl or ethoxycarbonyl, optionally substituted, such as N-mono-lower alkylated or N,N-di-lower alkylated, carbamoyl, for example N-methylcarbamoyl or N,N-dimethylcarbamoyl, or cyano as well as oxo or oxido, it being possible for one or more such substituents, which are bonded above all to ring carbon atoms but also, especially lower alkyl and oxido, to ring nitrogen atoms, to be present.

Such heterocyclic radicals are above all monocyclic, five-membered diaza-, triaza-, tetraza-, thiaza-, thiadiaza-, thiatriaza-, oxaza- or oxadiaza-cyclic radicals of aromatic character which are optionally substituted, for example which contain the abovementioned substituents, especially lower alkyl, for example methyl, or corresponding radicals with a fused benzene ring, such as benzodiaza- or benzooxazacyclic radicals, which are optionally substituted, for example which contain the abovementioned substituents, monocyclic, six-membered monoaza- or diaza-cyclic radicals of aromatic character which are optionally substituted, for example which contain the abovementioned substituents, above all oxido, or corresponding partially saturated radicals which are optionally substituted, for example which contain the abovementioned substituents, above all oxo, or bicyclic triaza- or tetraza-cyclic radicals of aromatic character which are optionally substituted, for example which contain the abovementioned substituents, or corresponding partially saturated radicals which are optionally substituted, for example which contain the abovementioned substituents, above all oxo.

Preferred mercapto groups $R_2$ which are etherified with a heterocyclic radical and wherein the heterocyclic radical represents a corresponding monocyclic, five-membered radical or a corresponding benzoheterocyclic radical are, inter alia, imidazolylthio, for example 2-imidazolylthio, triazolylthio which is optionally substituted by lower alkyl and/or phenyl, for example 1-methyl-1H-1,2,3-triazol-4-ylthio, 1H-1,2,4-triazol-3-ylthio, 5-methyl-1H-1,2,4-triazol-3-ylthio, 3-methyl-1-phenyl-1H-1,2,4-triazol-5-ylthio, 4,5-dimethyl-4H-1,2,4-triazol-3-ylthio or 4-phenyl-4H-1,2,4-triazol-3-ylthio, tetrazolylthio which is optionally substituted by lower alkyl, phenyl or halogenophenyl, for example 1H-tetrazol-5-ylthio, 1-methyl-1H-tetrazol-5-ylthio, 1-phenyl-1H-tetrazol-5-ylthio or 1-(4-chlorophenyl)-1H-tetrazol-5-ylthio, thiazolylthio or isothiazolylthio which are optionally substituted by lower alkyl or thienyl, for example 2-thiazolylthio, 4-(2-thienyl)-2-thiazolylthio, 4,5-dimethyl-2-thiazolylthio, 3-isothiazolylthio, 4-isothiazolylthio or 5-isothiazolylthio, thiadiazolylthio which is optionally substituted by lower alkyl, for example 1,2,3-thiadiazol-4-ylthio, 1,2,3-thiadiazol-5-ylthio, 1,3,4-thiadiazol-2-ylthio, 2-methyl-1,3,4-thiadiazol-5-ylthio, 1,2,4-thiadiazol-5-ylthio or 1,2,5-thiadiazol-3-ylthio, thiatriazolylthio, for example 1,2,3,4-thiatriazol-5-ylthio, oxazolylthio or isoxazolylthio which are optionally substituted by lower alkyl or phenyl, for example 5-oxazolylthio, 4-methyl-5-oxazolylthio, 2-oxazolylthio, 4,5-diphenyl-2-oxazolylthio or 3-methyl-5-isoxazolylthio, oxadiazolylthio which is optionally substituted by lower alkyl, phenyl, nitrophenyl or thienyl, for example 1,2,4-oxadiazol-5-ylthio, 2-methyl-1,3,4-oxadiazol-5-ylthio, 2-phenyl-1,3,4-oxadiazol-5-ylthio, 5-(4-nitrophenyl)-1,3,4-oxadiazol-2-ylthio or 2-(thienyl)-1,3,4-oxadiazol-5-ylthio, benzimidazolylthio which is optionally substituted by halogen, for example 2-benzimidazolylthio or 5-chloro-2-benzimidazolylthio, or benzoxazolylthio which is optionally substituted by halogen or nitro, for example 2-benzoxazolylthio, 5-nitro-2-benzoxazolylthio or 5-chloro-2-benzoxazolylthio.

Preferred mercapto groups $R_2$ which are etherified with a heterocyclic radical and wherein the heterocyclic radical represents a corresponding monocyclic, six-membered radical or a corresponding partially saturated radical are, inter alia, 1-oxido-pyridylthio which is optionally substituted by halogen, for example 1-oxido-2-pyridylthio or 4-chloro-1-oxido-2-pyridylthio, pyridazinylthio which is optionally substituted by hydroxyl, for example 3-hydroxy-6-pyridazinylthio, N-oxido-pyridazinylthio which is optionally substituted by lower alkyl, lower alkoxy or halogen, for example 2-oxido-6-pyridazinylthio, 3-chloro-1-oxido-6-pyridazinylthio, 3-methyl-2-oxido-6-pyridazinylthio, 3-methoxy-1-oxido-6-pyridazinylthio, 3-ethoxy-1-oxido-6-pyridazinylthio, 3-n-butoxy-1-oxido-6-pyridazinylthio or 3-(2-ethylhexyloxy)-1-oxido-6-pyridazinylthio, or 2-oxo-1,2-dihydro-pyrimidinylthio which is optionally substituted by lower alkyl, amino, dilower alkylamino or carboxyl, for example 2-oxo-1,2-dihydro-4-pyrimidinylthio, 6-methyl-2-oxo-1,2-dihydro-4-pyrimidinylthio, 5-methyl-2-oxo-1,2-dihydro-4-pyrimidinylthio, 6-amino-2-oxo-1,2-dihydro-4-pyrimidinylthio, 6-dimethylamino-2-oxo-1,2-dihydro-4-pyrimidinylthio, 5-carboxy-2-oxo-1,2-dihydro-4-pyrimidinylthio or 6-carboxy-2-oxo-1,2-dihydro-4-pyrimidinylthio.

Preferred mercapto groups $R_2$ which are etherified with a heterocyclic radical and wherein the heterocyclic radical represents a corresponding bicyclic radical which is optionally partially saturated are, inter alia, triazolopyridylthio, for example s-triazolo[4,3-a]pyrid-3-ylthio or 3H-v-triazolo[4,5-b]pyrid-5-ylthio, or purinylthio which is optionally substituted by halogen and/or lower alkyl, for example 2-purinylthio, 6-purinylthio or 8-chloro-2-methyl-6-purinylthio, as well as 2-oxo-1,2-dihydro-purinylthio, for example 2-oxo-1,2-dihydro-6-purinylthio.

Hydroxyl groups $R_2$ esterified with aliphatic carboxylic acids are, in particular, lower alkanoyloxy, especially acetoxy and also formyloxy, propionyloxy, valeryloxy, hexanoyloxy, heptanoyloxy or pivaloyloxy.

An esterified hydroxyl group $R_2$ is also a hydroxyl group esterified by an optionally N-substituted half-amide of carbonic acid. N-Substituents are lower alkyl which optionally contains halogen, for example chlorine, for example methyl, ethyl or 2-chloroethyl, or lower alkanoyl, for example acetyl or propionyl. Hydroxyl groups $R_2$ esterified in this way are, for example, carbamoyloxy, N-methylcarbamoyloxy, N-ethylcarbamoyloxy, N-(2-chloroethyl)-carbamoyloxy or N-acetylcarbamoyloxy.

A mercapto group esterified by a heterocyclic carboxylic acid contains, as the heterocyclic radical, for example one of the heterocyclic radicals mentioned above in connection with the etherified mercapto groups and also designated as preferred. Mercapto groups esterified in this way are, in particular, triazolylcarbonylthio which is optionally substituted by lower alkyl and/or phenyl, for example 1-methyl-1H-1,2,3-triazol-4-ylcarbonylthio, thiazolylcarbonylthio or isothiazolylcarbonylthio which are optionally substituted by lower alkyl or thienyl, for example 3-isothiazolylcarbonylthio, 4-isothiazolylcarbonylthio or 5-isothiazolyl-carbonylthio, thiadiazolylcarbonylthio which is optionally substituted by lower alkyl, for example 1,2,3-thiadiazol-4-ylcarbonylthio, 1,2,3-thiadiazol-5-ylcarbonylthio or 1,2,5-thiadiazol-3-ylcarbonylthio, or oxazolylcarbonylthio or isoxazolylcarbonylthio which are optionally substituted by lower alkyl or phenyl, for example 3-methyl-5-isoxazolylcarbonylthio.

In a quaternary ammonium group $R_2$, which is derived from a tertiary organic base, the nitrogen atom is bonded to the methyl carbon atom and accordingly is present in the quaternised, positively charged form. Quaternary ammonium groups are, inter alia, tri-lower alkylammonium, for example trimethylammonium, triethylammonium, tripropylammonium or tributylammonium, but especially optionally substituted sulphonamido, for example sulphonamido substituted by lower alkyl, such as methyl, hydroxy-lower alkyl, such as hydroxymethyl, or amino, such as 4-aminophenylsulphonamido, hydroxyl, halogen, such as fluorine, chlorine, bromine or iodine, halogeno-lower alkyl, such as trifluoromethyl, sulpho, optionally functionally modified carboxyl, such as carboxyl, lower alkoxycarbonyl, for example methoxycarbonyl, cyano, carbamoyl which is optionally N-monosubstituted or N,N-disubstituted by lower alkyl, for example methyl or ethyl, or hydroxy-lower alkyl, for example hydroxymethyl, for example carbamoyl, N-methylcarbamoyl or N,N-dimethylcarbamoyl, hydrazinocarbonyl which is optionally N-substituted by lower alkyl, for example hydrazinocarbonyl, carboxy-lower alkyl, such as carboxymethyl, lower alkanoyl, such as acetyl, or 1-lower alkylpyrrolidinyl, such as 1-methyl-2-pyrrolidinyl, or monosubstituted or polysubstituted, monocyclic or bicyclic azacyclic ammonium groups of aromatic character with 1 or 2 ring nitrogen atoms and optionally one ring sulphur atom, such as pyrimidinium, pyridazinium, thiazolium, quinolinium and, above all, pyridinium.

Heterocyclic ammonium groups $R_2$ are, above all, sulphonamido which is optionally substituted by lower alkyl or hydroxy-lower alkyl, or hydroxyl, halogen, trifluoromethyl, sulpho, carboxyl, lower alkoxycarbonyl, cyano, lower alkanoyl, 1-lower alkyl-pyrrolidinyl or pyridinium which optionally contains carbamoyl which is N-substituted by lower alkyl or hydroxy-lower alkyl, for example pyridinium, 2-, 3- or 4-methyl-pyridinium, 3,5-dimethyl-pyridinium, 2,4,6-trimethyl-pyridinium, 2-, 3- or 4-ethyl-pyridinium, 2-, 3- or 4-propylpyridinium or especially 4-hydroxymethyl-pyridinium, also 2-amino-pyridinium or 2-amino-6-methyl-pyridinium, 2-(4-aminophenylsulphonylamido)-pyridinium, 3-hydroxy-pyridinium, 3-fluoro-, 3-chloro-, 3-iodo- or especially 3-bromo-pyridinium, 4-trifluoromethyl-pyridinium, 3-sulpho-pyridinium, 2-, 3- or 4-carboxy-pyridinium or 2,3-dicarboxy-pyridinium, 4-methoxycarbonyl-pyridinium, 3- or 4-cyano-pyridinium, 3-carboxymethyl-pyridinium, 3- or 4-acetyl-pyridinium, 3-(1-methyl-2-pyrrolidinyl)-pyridinium and especially 4-carbamoyl-pyridinium as well as 3-carbamoyl-, 3- or 4-N-methylcarbamoyl-, 4-N,N-dimethylcarbamoyl-, 4-N-ethylcarbamoyl-, 3-N,N-diethylcarbamoyl-, 4-N-propylcarbamoyl-, 4-isopropylcarbamoyl- and 4-hydroxymethylcarbamoyl-pyridinium, and also optionally correspondingly substituted pyrimidinium, pyridazinium, thiazolium or quinolinium.

In an esterified carboxyl group of the formula —C(=O)—R, which is splittable under physiological conditions, R is, above all, an acyloxymethoxy group, wherein acyl denotes, for example, the radical of an organic carboxylic acid, above all of an optionally substituted lower alkanecarboxylic acid, or wherein acyloxymethyl forms the radical of a lactone. Such groups $R_2$ are lower alkanoyloxymethoxy, for example acetoxymethoxy or pivaloyloxymethoxy, amino-lower-alkanoyloxy methoxy, especially α-amino-lower alkanoyloxymethoxy, for example glycyloxymethoxy, L-valyloxymethoxy or L-leucyloxymethoxy, and also phthalidyloxy, for example 2-phthalidyloxy, or indanyloxy, for example 5-indanyloxy.

Salts are, in particular, those of compounds of the formula I having a free carboxyl group —C(=O)—R, above all metal salts or ammonium salts, such as alkali metal salts and alkaline earth metal salts, for example sodium salts, potassium salts, magnesium salts or calcium salts, as well as ammonium salts with ammonia or suitable organic amines, it being possible to use, for formation of the salt, above all aliphatic, cycloaliphatic, cycloaliphatic-aliphatic or araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)amine or tris-(2-hydroxyethyl)-amine, basic aliphatic esters of carboxylic acids, for example 4-aminobenzoic acid 2-diethylaminoethyl ester, lower alkyleneamines, for example 1-ethyl-piperidine, cycloalkylamines, for example dicyclohexylamine, or benzylamines, for example N,N'-dibenzyl-ethylenediamine, and also bases of the pyridine type, for example pyridine, collidine or quinoline. Compounds of the formula I can also form acid addition salts, for example with inorganic acids, such as hydrochloric acid, sulphuric acid or phosphoric acid, or with suitable organic carboxylic acids or sulphonic acids, for example trifluoroacetic acid, as well as with amino-acids, such as arginine and lysine. Compounds of the formula I having a free carboxyl group can also be present in the form of inner salts, that is to say in the zwitterionic form.

The compounds of the formula I and their pharmaceutically usable, non-toxic salts are valuable substances which have an antibiotic action and which can be used especially as antibacterial antibiotics. For example, they are active against micro-organisms, such as Gram-positive bacteria, for example against *Staphylococcus aureus* (in vitro in minimum concentrations of about 0.0005 mg/ml), including penicillin-resistant *Staphylococcus aureus* (in vitro in minimum concentrations of about 0.001 mg/ml), and also against *Bacillus subtilis* (in vitro in minimum concentrations of about 0.0002 mg/ml) and against Gram-negative bacteria, for example against *Escherichia coli* (in vitro in minimum concentrations of about 0.001 mg/ml), including ampicillin-resistant, carbenicillin-resistant and rifamycin-resistant *Escherichia coli* (in vitro in minimum concentrations of about 0.002 mg/ml), and also against *Klebsiella pneumoniae* and *Salmonella typhimurium*, including ampicillin-resistant, carbenicillin-resistant and rifamycin-resistant *Salmonella typhimurium* (in vitro in minimum concentrations of about 0.0006 mg/ml), *Proteus vulgaris, Proteus mirabilis*, including carbenicillin-resistant *Proteus mirabilis*, and *Proteus rettgeri* (in vitro in minimum concentrations of about 0.005 mg/ml) as well as *Proteus morganii* (in vitro in minimum concentrations of about 0.03 mg/ml). The new compounds are distinguished by an excellent stability against β-lactamases, such as cephalosporinases, especially from Gram-negative bacteria, which can be shown by means of the rates of hydrolysis in the presence of β-lactamases isolated from various Gram-negative germs, such as *Escherichia coli, Aerobacter cloacae, Proteus morganii* and *Pseudomonas aeruginosa*. The rates at which the new compounds are hydrolysed by β-lactamases are, for example, more than a hundred times smaller than those of cephalothin and cephaloridin. The new compounds can thus be used accordingly, for example in the form of antibiotically active preparations, for the treatment of infections caused by Gram-positive or Gram-negative bacteria.

The present invention relates above all to those compounds of the formula I, wherein Am represents unsubstituted amino, lower alkylamino or di-lower alkylamino, wherein lower alkyl contains up to 4 carbon atoms, or represents lower alkyleneamino, wherein lower alkylene contains 4 to 6 chain carbon atoms, X represents oxygen or especially sulphur and also represents ethenylene of the formula —CH=CH— and the Am-methyl-substituted radical represents Am-methyl-2-thienyl, such as 4- or 5- and also 3-Am-methyl-2-thienyl, as well as Am-methyl-3-thienyl, or Am-methyl-2-furyl, such as 4- or 5- as well as 3-Am-methyl-2-furyl, and also Am-methyl-3-furyl, or Am-methyl-phenyl, for example 2- or 4-Am-methyl-phenyl, and the grouping of the formula —S—A— represents a radical of the formula Ia but especially a radical of the formula Ib, wherein $R_1$ denotes lower alkoxy, preferably with up to 4 carbon atoms, or the group of the formula —CH$_2$—R$_2$, and $R_2$ represents hydrogen, lower alkanoyloxy, especially acetoxy, optionally substituted carbamoyloxy, etherified mercapto or quaternary ammonium, and wherein R represents hydroxyl, as well as salts, especially the non-toxic, pharmaceutically usable salts, in particular the alkali metal or alkaline earth metal salts, as well as the inner salts, of such compounds.

The present invention relates above all to compounds of the formula I, wherein Am denotes unsubstituted amino, lower alkylamino or di-lower alkylamino, wherein lower alkyl contains up to 4 carbon atoms, X represents oxygen or especially sulphur and also represents ethenylene of the formula —CH=CH—, and the Am-methyl-substituted radical represents Am-methyl-2- or -3-thienyl, for example 4- or 5- and also 3-Am-methyl-2-thienyl, as well as Am-methyl-2-furyl, for example 4- or 5-Am-methyl-2-furyl, as well as Am-methyl-phenyl, for example 2- or 4-Am-methyl-phenyl, and the grouping of the formula —S—A— represents a radical of the formula Ia or Ib, wherein $R_1$ denotes lower alkoxy with up to 4 carbon atoms, such as methoxy, or the group of the formula —CH$_2$—R$_2$, and $R_2$ denotes hydrogen, lower alkanoyloxy, for example acetoxy, optionally N-lower alkylated, as well as N-halogeno-lower alkylated, carbamoyloxy, for example carbamoyloxy, methylcarbamoyloxy, ethylcarbamoyloxy or 2-chloroethyl-carbamoyloxy, lower alkylthio, for example methylthio, optionally substituted heterocyclylthio, wherein heterocyclyl represents a monocyclic five-membered heterocyclic radical of aromatic character which is bonded to the thio sulphur atom via a ring carbon atom and which contains 2 or 3 ring nitrogen atoms and optionally additionally a ring oxygen atom, a ring sulphur atom or a ring nitrogen atom, it being possible for such a radical to be optionally substituted by lower alkyl, especially methyl, or wherein heterocyclyl represents an unsaturated monocyclic, six-membered heterocyclic radical, which is bonded to the thio sulphur atom via a ring carbon atom and which contains 2 ring nitrogen atoms, and in which either a ring nitrogen atom carries an oxido group or a ring carbon atom carries an oxo group, it being possible for such a heterocyclyl radical to be optionally substituted by lower alkyl, for example methyl, lower alkoxy, for example methoxy, or halogen, for example chlorine, or $R_2$ denotes a pyridinium radical, which can be optionally substituted by halogen, for example chlorine or bromine, lower alkyl, for example methyl or ethyl (preferably in the 4-position), carboxyl, carbamoyl or hydrazinocarbonyl, and wherein R represents hydroxyl, as well as salts, especially pharmaceutically usable, non-toxic salts, in particular the alkali metal salts or alkaline earth metal salts, as well as the inner salts, of such compounds.

The invention relates especially to 3-cephem compounds of the formula I, wherein Am represents unsubstituted amino, methylamino or dimethylamino, X above all represents sulphur and also oxygen, and the Am-methyl-substituted radical denotes Am-methyl-2-thienyl or Am-methyl-2-furyl, for example 4- or preferably 5- and also 3-Am-methyl-2-thienyl or 4- or 5-Am-methyl-2-furyl, and the grouping of the formula -S-A- denotes the radical of the formula Ib, wherein $R_1$ represents lower alkoxy with up to 4 carbon atoms, especially methoxy, or represents the radical of the formula —CH$_2$—R$_2$, in which $R_2$ denotes hydrogen, acetoxy, carbamoyloxy, N-lower alkyl-carbamoyloxy, for example methylcarbamoyloxy or ethylcarbamoyloxy, N-halogeno-lower alkylcarbamoyloxy, for example 2-chloroethylcarbamoyloxy, lower alkylthio, for example methylthio, thiadiazolylthio which is optionally substituted by lower alkyl, for example methyl and which is bonded to the thio sulphur atom via a ring carbon atom, for example 1,3,4-thiadiazol-2-ylthio, 5-methyl-1,3,4-thiadiazol-2-ylthio or 5-methyl-1,2,4-thiadiazol-2-ylthio, or tetrazolylthio, for example 1-methyl-5-tetrazolylthio, N-oxido-pyridazinylthio which is optionally substituted by lower alkyl, for example methyl, lower alkoxy, for example methoxy, or halogen, for example chlorine, and which is bonded to the thio sulphur atom via a ring carbon atom, for example 3-methyl-2-oxido-6-pyridazinylthio, 3-methoxy-1-oxido-6-pyridazinylthio or 3-chloro-1-oxido-6-pyridazinylthio, or pyridinium which is optionally substituted by carbamoyl, for example pyridinium or 3-carbamoyl-pyridinium, and wherein the group R represents hydroxyl, as well as salts, especially the non-toxic, pharmaceutically usable salts, in particular the alkali metal salts or alkaline earth metal salts, as well as the inner salts, of such compounds.

The invention relates above all to 3-cephem compounds of the formula I, wherein Am denotes amino, methylamino or dimethylamino, X above all represents sulphur and also oxygen, and the Am-methyl-substituted radical denotes Am-methyl-2-thienyl or Am-methyl-2-furyl, for example 4- or preferably 5- as well as 3-Am-methyl-2-thienyl or -2-furyl, and the grouping of the formula -S-A- denotes the radical of the formula Ib, wherein $R_1$ represents methoxy or the radical of the formula —$CH_2R_2$, in which $R_2$ denotes hydrogen, acetoxy, carbamoyloxy, methylcarbamoyloxy, ethylcarbamoyloxy, 2-chloroethylcarbamoyloxy, methylthio, 5-methyl-1,3,4-thiadiazol-2-ylthio or 1-methyl-5-tetrazolylthio, and wherein R represents hydroxyl, as well as salts, especially the non-toxic, pharmaceutically usable salts, in particular the alkali metal salts or alkaline earth metal salts, as well as the inner salts, of such compounds The invention relates especially to the compounds described in the examples and to their salts, especially the non-toxic, pharmaceutically usable salts, such as the alkali metal salts or alkaline earth metal salts, and above all to their inner salts, which, in the indicated doses, exhibit outstanding antibiotic actions and which accordingly are used in the form of antibiotically active preparations.

The new compounds of the present invention can be manufactured in a manner which is in itself known when, for example, the amino group in a compound of the formula

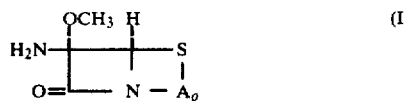 (II)

wherein the amino group can be optionally substituted by a group which permits the acylation, and wherein the grouping of the formula -S-$A_o$- denotes a radical of the formula

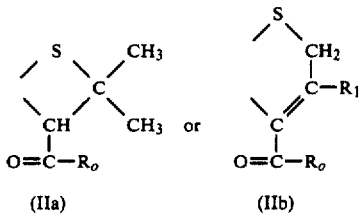

(IIa)   (IIb)

wherein $R_o$ has the meaning of R or represents a carboxyl protective radical which, with the carbonyl group of the formula —C(=O)—, forms a protected carboxyl group, or in a salt thereof, is acylated by treatment with an acid of the formula

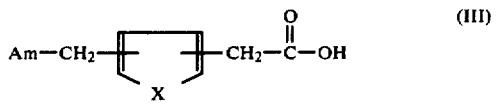 (III)

wherein an amino group Am, if necessary, is present in the protected form, or with a reactive functional acid derivative thereof or with a salt of such a compound and, in a resulting compound, a protected amino group in the Am-methyl radical is converted into the group Am and/or, if desired or necessary, a carboxyl group of the formula —C(=O)—$R_o$ is converted into a carboxyl group of the formula —C(=O)—R, and/or, if desired, in a resulting compound of the formula I, an amino group Am is converted into another amino group Am and/or, if desired, a group $R_1$ is converted into another group $R_1$ and/or, if desired, a resulting salt is converted into the free compound or into another salt or a resulting free compound is converted into a salt.

Radicals which substitute the amino group and permit acylation thereof and which are optionally present in a starting material of the formula II are, for example, organic sily or stannyl groups and also ylidene groups, which, together with the amino group, form a Schiff's base. The organic silyl or stannyl groups mentioned are, for example, the same as those which, with the carboxyl group on the penam or cephem ring, are also able to form a protected carboxyl group —C(=O)—$R_o$. On silylation or stannylation of a carboxyl group in a starting material of the formula II, the amino group can also be silylated or stannylated when an excess of the silylating or stannylating agent is used.

The ylidene groups mentioned are, above all, arylmethylene groups, wherein aryl represents, in particular, a carbocyclic, above all monocyclic, aryl radical, for example phenyl which is optionally substituted, such as by nitro or hydroxyl; such arylmethylene groups are, for example, benzylidene, 2-hydroxybenzylidene or 4-nitrobenzylidene and also oxacycloalkylidene which is optionally substituted, for example by carboxyl, for example 3-carboxy-2-oxacyclohexylidene.

A protected carboxyl group of the formula —C(=O)—$R_o$ in a starting material of the formula II is above all an esterified carboxyl group which preferably can be split easily, wherein $R_o$ represents an etherified hydroxyl group, or a carboxyl group present in the form of an anhydride, wherein $R_o$ denotes an esterified, and especially a phosphorylated, hydroxyl group.

An etherified hydroxyl group $R_o$ which, in the starting material of the formula II, with the carbonyl grouping of the formula —C(=O)—, forms an esterified carboxyl group which preferably can be split easily, is, for example, a lower alkoxy group which preferably is substituted, above all in the α-position and also in the β-position, and/or is branched in the α-position. Substituents of such a group are, for example, carbocyclic aryl, such as phenyl which is optionally substituted, for example by lower alkyl, such as tert.-butyl, phenyl, hydroxyl, lower alkoxy, such as methoxy, and/or nitro, furyl, such as 2-furyl, aryloxy, such as phenyloxy which is optionally substituted, for example by lower alkoxy, such as methoxy, arylcarbonyl, such as benzoyl which is optionally substituted, for example by halogen, such as bromine, cyano or acylamino, such as diacylamino, for example phthalimino or succinylimino; such substituents are preferably in the α-position of the lower alkoxy group $R_o$, it being possible for the latter, depending on the nature of the substituents, to contain one, two or more such radicals. Further substituents which are preferably in the β-position of the lower alkoxy radical $R_o$ are halogen, for example chlorine, bromine or iodine, an individual chlorine or bromine in such radicals being readily convertible into iodine before a carboxyl group protected in this way is liberated. Examples of the abovementioned, optionally substituted lower alkoxy groups $R_o$ are tert.-lower alkoxy, for example tert.-butoxy or tert.-pentoxy, α-phenyl-lower alkoxy which is optionally substituted in the phenyl radical, for example as indicated, such as benzyloxy, 4-hydroxy-3,5-di-tert.-butyl-benzyloxy, 2-biphenylyl-2-propyloxy, 4-methoxy-benzyloxy, 4,5-dimethoxy-2-nitro-benzyloxy or 4-nitro-benzyloxy, diphenylmethoxy which is optionally substituted in the phenyl radicals, for example as indicated, especially by lower alkoxy, for example methoxy, such as benzhydryloxy or 4,4'-dimethylmethoxy, as well as trityloxy, bis-phenyloxy-methoxy which is optionally substituted in the phenyl radicals, for example as indicated, especially by lower alkoxy, such as bis-4-methoxyphenyloxymethoxy, phenacyloxy which is optionally substituted, especially by halogen, such as phenacyloxy or 4-bromo-phenacyloxy, cyanomethoxy, diacyliminomethoxy, such as phthalyliminomethoxy or succinyliminomethoxy, or 2-halogeno-lower alkoxy, such as 2,2,2-trichloroethoxy, 2-bromoethoxy or 2-iodoethoxy.

Furthermore, an etherified hydroxyl group $R_o$ which, with the carbonyl grouping of the formula $-C(=O)-$, forms an esterified carboxyl group which preferably can be split easily, can also denote a cycloalkoxy group, the α-position of which preferably represents a bridge head carbon atom. A cycloalkoxy group $R_o$ of this type is, for example, 1-adamantyloxy.

Further etherified hydroxyl groups which represent the radical $R_o$ are organic silyloxy or stannyloxy groups, wherein organic radicals, 1 to 3 of which can be present, are especially optionally substituted aliphatic hydrocarbon radicals, such as lower alkyl, for example methyl, ethyl, n-propyl or tert.-butyl, or halogeno-lower alkyl, for example chloromethyl or 2-chloroethyl, as well as optionally substituted cycloaliphatic, aromatic or araliphatic hydrocarbon radicals, such as cycloalkyl, phenyl or phenyl-lower alkyl and also functional groups with organic substituents, such as etherified hydroxyl groups, for example lower alkoxy, such as methoxy or ethoxy, these silyloxy or stannyloxy groups being able optionally to contain, as further substituents, for example halogen, such as chlorine. Such radicals $R_o$ are, inter alia, tri-lower alkylsilyloxy, for example trimethylsilyloxy or tert.-butyldimethylsilyloxy, lower alkoxy-lower alkyl-halogeno-silyloxy, for example chloromethoxymethylsilyloxy, or tri-lower alkylstannyloxy, for example tri-n-butylstannyloxy.

The group $R_o$ can also represent a phosphoryloxy group which contains a substituted trivalent or pentavalent phosphorus atom and which, together with the carboxyl grouping of the formula $-C(=O)-$, forms a protected carboxyl group. Substituents of trivalent phosphorus, which can be identical or different, are, inter alia, optionally substituted hydrocarbon radicals, such as corresponding aliphatic or araliphatic hydrocarbon radicals, for example lower alkyl or halogenolower alkyl, such as methyl, ethyl or chloromethyl, or phenyl-lower alkyl, such as benzyl, etherified hydroxyl or mercapto groups, such as hydroxyl or mercapto groups etherified by optionally substituted aliphatic, aromatic or araliphatic hydrocarbon radicals, for example lower alkoxy or lower alkylthio, such as methoxy, ethoxy, methylthio or n-butylthio, phenyloxy or phenylthio which are optionally substituted, for example by lower alkyl, lower alkoxy or halogen, or phenyl-lower alkoxy or phenyl-lower alkylthio which are optionally substituted, for example by lower alkyl, lower alkoxy or halogen, for example benzyloxy or benzylthio, halogen, for example fluorine, chlorine or bromine, and/or a divalent hydrocarbon radical which is optionally substituted and/or interrupted by hetero-atoms, such as oxygen or sulphur, such as a corresponding aliphatic or araliphatic radical, for example lower alkylene, such as 1,4-butylene or 1,5-pentylene, 1-oxa-lower alkylene, wherein the second methylene group which is bonded to the phosphorus atom can also optionally be replaced by an oxygen atom or sulphur atom, for example 1-oxa-1,4-pentylene, 1-oxa-1,5-pentylene or 1,5-dioxa-1,5-pentylene, or two hydroxyl groups which are etherified by a divalent, optionally substituted hydrocarbon radical, such as a corresponding aliphatic, aromatic or araliphatic radical, such as lower alkylene or 1,2-phenylene. Substituents of pentavalent phosphorus are those of trivalent phosphorus and additionally an oxo group.

In a starting material of the formula II any further free functional groups which may be present in addition to the carboxyl group of the formula $-C(=O)-R_o$, such as a free hydroxyl group $R_2$, are, if desired or necessary, customarily present, during the acylation reaction, in a protected, preferably easily splittable, form; a free hydroxyl group can be present, for example, in an easily splittable etherified or esterified form, for example in the form of a lower alkoxy group, for example a methoxy group, or a 2-oxacycloalkoxy group, for example a 2-tetrahydropyranyloxy group, or, respectively, in the form of an acyloxy group, such as a lower alkanoyloxy group, for example an acetyloxy group, or a suitable etherified hydroxycarbonyloxy group.

In a starting material of the formula III, a secondary amino group Am, in particular, is advantageously protected by any one of the amino protective groups, preferably the easily removable amino protective groups, which are known in peptide chemistry or in penicillin and cephalosporin chemistry. Such protective groups can be, for example, acyl, arylmethyl, 2-carbonyl-1-vinyl, arylthio or aryl-lower alkylthio groups and also arylsulphonyl groups as well as organic silyl or stannyl groups. The starting material of the formula III can also be used in the form of an acid addition salt, in which the amino group Am is protected in the ionic form.

An easily removable acyl group is, for example, the formyl group or the acyl radical of a half-ester of carbonic acid, such as a lower alkoxycarbonyl group which preferably has multiple aliphatic substituents or branching and/or aromatic or hetero-aromatic substituents on the carbon atom in the α-position to the oxy group, or a methoxycarbonyl group which is substituted by an arylcarbonyl radical, especially a benzoyl radical, or a lower alkoxycarbonyl group which is substituted in the β-position by halogen, such as tert.-lower alkoxycarbonyl, for example tert.-butoxycarbonyl or tert.-pentyloxycarbonyl, arylcarbonylmethoxycarbonyl, for example phenacyloxycarbonyl, 2-halogenoethoxycarbonyl, for example 2,2,2-trichloroethoxycarbonyl or 2-iodoethoxycarbonyl, or a group which can be converted into the latter, such as 2-chloroethoxycarbonyl or 2-bromoethoxycarbonyl, and also preferably polycyclic cycloalkoxycarbonyl, for example adamantyloxycarbonyl, phenyl-lower alkoxycarbonyl, especially α-phenyl-lower alkoxycarbonyl, which is optionally substituted, for example by lower alkyl, such as tert.-butyl, hydroxyl, lower alkoxy, such as methoxy and/or nitro, for example 4-methoxy-benzyloxycarbonyl, 4-hydroxy-3,5-bis-tert.-butylbenzyloxycarbonyl, 4-nitrobenzyloxycarbonyl or α-4-biphenylyl-α-methylethoxycarbonyl, and also diphenylmethoxycarbonyl which is optionally substituted, for example by lower alkoxy, such as methoxy, for example diphenylmethoxycarbonyl, or furyllower alkoxycarbonyl, above all α-furyl-lower alkoxycarbonyl, for example furfuryloxycarbonyl. An acyl group for the protection of an amino group Am can also be the corresponding radical of a suitable carboxylic acid, such as an aryldicarboxylic acid, for example the phthaloyl radical, or of a halogeno-lower alkanecarboxylic acid, for example the trifluoroacetyl radical.

Examples of easily removable arylmethyl groups which may be mentioned are optionally substituted polyarylmethyl groups, such as diarylmethyl or triarylmethyl groups, for example trityl which is optionally substituted, such as by lower alkyl, for example methyl, and/or lower alkoxy, such as methoxy, in particular optionally o- and/or p-methoxy-substituted trityl.

Easily removable 2-carbonyl-1-vinyl groups, which together with the amino group form an enamine, are, for example, 2-lower alkoxycarbonyl-1-lower alkylvinyl groups, especially the 2-methoxycarbonyl-1-methyl-1-vinyl group.

Easily removable arylthio or aryl-lower alkylthio groups are, for example, substituted phenylthio groups, for example phenylthio groups substituted by nitro or halogen, for example chlorine, such as the 2-nitrophenylthio group, the 2,4-dinitrophenylthio group or the pentachlorophenylthio group, and also triarylmethylthio groups, for example the triphenylmethylthio group.

An easily removable organic silyl or stannyl group can preferably carry as substituents optionally substituted hydrocarbon radicals, especially aliphatic hydrocarbon radicals, such as lower alkyl, for example methyl, ethyl or tert.-butyl, or halogeno-lower alkyl, for example 2-chloroethyl, and also functional groups, for example etherified or esterified hydroxyl groups, such as lower alkoxy, for example methoxy or ethoxy, or halogen, for example chlorine. Such silyl or stannyl radicals are, inter alia, tri-lower alkylsilyl, for example trimethylsilyl or tert.-butyldimethylsilyl, lower alkoxy-lower alkyl-halogeno-silyl, for example chloromethoxymethylsilyl, or tri-lower alkylstannyl, for example tri-n-butylstannyl.

The acylation of the free amino group or of an amino group substituted by a radical which permits acylation, can be carried out in a known manner by treatment with an acid of the formula III or a reactive functional derivative thereof.

If a free acid of the formula III, preferably having a protected amino group Am, is employed for the the acylation, suitable condensing agents are customarily used, such as carbodimides, for example N,N'-diethyl-, N,N'-dipropyl-, N,N'-diisopropyl-, N,N'-dicyclohexyl- or N-ethyl-N'-3-dimethylaminopropyl-carbodiimide, suitable carbonyl compounds, for example carbonyldiimidazole, or isoxazolinium salts, for example N-ethyl-5-phenyl-isoxazolinium-3'-sulphonate and N-tert.-butyl-5-methyl-isoxazolinium perchlorate, or an acylamino compound, for example 2-ethoxy-1-ethoxycarbonyl-1,2-dihydroquinoline.

The condensation reaction is preferably carried out in an anhydrous reaction medium, preferably in the presence of a solvent or diluent, for example methylene chloride, dimethylformamide or acetonitrile, and, if desired or necessary, with cooling or heating and/or in an inert gas atmosphere.

An amide-forming functional derivative of an acid of the formula III, preferably having a protected amino group Am, is above all an anhydride of such an acid, including and preferably a mixed anhydride, but also an inner anhydride, that is to say the corresponding ketone. Mixed anhydrides are, for example, those with inorganic acids, such as with hydrogen halide acids, that is to say the corresponding acid halides, for example acid chlorides or acid bromides, and also with hydrozoic acid, that is to say the corresponding acid azides, with an acid containing phosphorus, for example phosphoric acid or phosphorous acid, or with an acid containing sulphur, for example sulphuric acid, or with hydrocyanic acid. Further mixed anhydrides are, for example, those with organic carboxylic acids, such as with lower alkanecarboxylic acids which are optionally substituted, for example by halogen, such as fluorine or chlorine, for example pivalic acid or trichloroacetic acid, or with half-esters, especially lower alkyl half-esters, of carbonic acid, such as the ethyl half-ester or the isobutyl half-ester of carbonic acid, or with organic, especially aliphatic or aromatic, sulphonic acids, for example p-toluenesulphonic acid.

Further acid derivatives of an acid of the formula III which are suitable for reaction with the amino group are activated esters, customarily with a protected amino group Am in the Am-methyl grouping, such as esters with vinylogous alcohols (that is to say enols), such as vinylogous lower alkenols, or aryl esters, such as 4-nitrophenyl esters or 2,4-dinitrophenyl esters, heteroaromatic esters, such as benztriazole esters, for example 2-benztriazole esters, or diacylimino esters, such as succinylimino esters or phthalylimino esters.

The acylation with an acid derivative, such as an anhydride, and especially with an acid halide, can be carried out in the presence of an acid-binding agent, for example of an organic base, such as an organic amine, for example a tertiary amine, such as a tri-lower alkylamine, for example trimethylamine, triethylamine or ethyl-diisopropylamine, or a N,N-di-lower alkyl-aniline, for example N,N-dimethylaniline, or a base of the pyridine type, for example pyridine, or of an inorganic base, for example an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate, or calcium hydroxide, carbonate or bicarbonate, or of an oxirane, for example a lower 1,2-alkylene oxide, such as ethylene oxide or propylene oxide.

The above acylation can be carried out in an inert, preferably anhydrous solvent or solvent mixture, for example in a carboxylic acid amide, such as a formamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at lowered or elevated temperature and/or in an inert gas atmosphere, for example a nitrogen atmosphere.

In an acid of the formula III, or in an acid derivative thereof, the amino group Am is customarily in the protected form, it also being possible for a protected amino group Am in a starting material of the formula III to be in the ionic form, that is say the starting material of the formula III is used in the form of an acid addition salt, preferably with a strong inorganic acid, such as a hydrogen halide acid, for example hydrochloric acid, or sulphuric acid.

Furthermore, if desired, an acid derivative can be formed in situ. Thus, for example, a mixed anhydride is obtained by treating an acid of the formula III, or a suitable salt thereof, such as an ammonium salt, with, for example, an organic amine, such as 4-methylmorpholine, or a metal salt, for example an alkali metal salt, with a suitable acid derivative, such as a corresponding acid halide of an optionally substituted lower alkanecarboxylic acid, for example trichloroacetyl chloride, or with a half-ester of a carbonic acid half-halide, for example the ethyl ester or isobutyl ester of chloroformic acid, and the mixed anhydride thus obtainable is used without isolation.

In a resulting compound, functional, optionally protected groups can be converted, if desired or necessary, in a manner which is in itself known into other functional groups, for example free functional groups. Above all, in a compound obtainable according to the invention, a protected amino group in the Am-methyl substituent of the acylamino grouping must be liberated and/or a protected carboxyl group of the formula —C(=O)—$R_o$, which is different from a carboxyl grouping of the formula —C(=O)—R, must be converted into a group of the formula —C(=O)—R; also, if desired, in a manner which is in itself known, a free carboxyl group of the formula —C(=O)—R can be converted into a physiologically splittable carboxyl group of the formula —C(=O)—R and/or a group $R_1$ in a grouping of the formula Ib can be converted into another group $R_1$. These conversions are carried out in a manner which is in itself known and multiple conversions can be carried out in any desired sequence, the latter usually depending on the nature of the radicals to be converted or to be split off and on the reactions used for this purpose. It is also possible simultaneously to convert more than one protected functional group into the corresponding free functional groups. Thus, for example, by treatment with a suitable acid, such as trifluoroacetic acid, optionally in the presence of anisole, it is possible, in a resulting compound, simultaneously to convert a tert.-butoxycarbonylamino group or a diphenylmethoxycarbonylamino group in the Am-methyl substituent of the acylamino radical in the 6- or 7-position and a diphenylmethoxycarbonyl group, which represents the radical of the formula —C(=O)—$R_o$, in the 3- or 4-position of a resulting penam compound or 3-cephem compound into the amino group and the carboxyl group respectively.

A protected amino group Am can be converted into an amino group Am in a manner which is in itself known, usually by solvolysis or reduction.

A formyl group, as an amino protective group, can be split off, for example by treatment with an acid agent, for example p-toluenesulphonic acid or hydrochloric acid, with a weakly basic agent; for example dilute ammonia, or with a decarbonylating agent, for example tris-(triphenylphosphine)rhodium chloride.

In a resulting compound, an easily removable acyl group, such as an α-poly-branched lower alkoxycarbonyl group, for example tert.-butoxycarbonyl, also a polycyclic cycloalkoxycarbonyl group, for example 1-adamantyloxycarbonyl, an optionally substituted diphenylmethoxycarbonyl group, for example diphenylmethoxycarbonyl, or an α-furyl-lower alkoxycarbonyl group can be split off from an acylamino group, for example, by acidolysis, such as treatment with a suitable acid, such as a strong, preferably aliphatic, carboxylic acid, for example an optionally halogenated, especially fluorinated, lower alkane carboxylic acid, above all formic acid or trifluoroacetic acid, optionally in the presence of a nucleophilic reagent, such as anisole, and a formyl group can be split off by treatment with a strong acid, such as a mineral acid, for example hydrochloric acid, or a strong organic sulphonic acid, for example 4-methylphenylsulphonic acid, and also by treatment with a decarbonylating agent, for example tris-triphenylphosphine-rhodium chloride, whilst, for example, a suitably substituted benzyloxycarbonyl group, such as 4-hydroxy-3,5-bis-tert.-butyl-benzyloxycarbonyl, can be removed, for example by treatment with an optionally anhydrous, weak base, such as an alkali metal salt of an organic carboxylic acid, for example the sodium salt or potassium salt of 2-ethyl-pentanecarboxylic acid, with an alkali metal salt of a thiophenol, for example the sodium salt of thiophenol, or with a suitable organic amine, for example ethylamine or cyclohexylamine, or a suitably substituted lower alkanoyl group, for example trifluoroacetyl, can be removed by hydrolysis under weakly basic conditions. A 2-halogeno-lower alkoxycarbonyl group, such as 2,2,2-trichloroethoxycarbonyl or 2-iodoethoxycarbonyl, or a phenacyloxycarbonyl group can be split off, for example by treatment with a chemical reducing agent, such as a suitable reducing metal or a corresponding metal compound, for example zinc, or a chromium-II compound, such as chromium-II chloride or chromium-II acetate, usually in the presence of an agent which, together with the metal or the metal compound, generates nascent hydrogen, and preferably in the presence of aqueous acetic acid. A phenacyloxycarbonyl group can also be replaced by hydrogen by treatment with a suitable nucleophilic, preferably salt-forming, reagent, such as sodium thiophenolate.

Furthermore, in a resulting compound, an amino group which is protected by a suitably substituted benzyloxycarbonyl group, such as 4-methoxy- or 4-nitrobenzyloxycarbonylamino, can be split reductively, such as hydrogenolytically, for example by treatment with hydrogen in the presence of a hydrogenation catalyst, for example palladium, and, in particular, 4-nitrobenzyloxycarbonylamino can be split by treatment with a chemical reducing agent, for example sodium dithionite.

A polyarylmethyl group, such as the trityl group, can be split off, for example, by treatment with an acid agent, such as a mineral acid, for example hydrochloric acid.

An amino group protected in the form of an enamine, and also an amino group protected by arylthio, aryllower alkylthio or arylsulphonyl, can be split, for example, by treatment with an acid agent, above all an aqueous acid, such as an organic carboxylic acid, for example formic acid, acetic acid or propionic acid, or a mineral acid, for example hydrochloric acid or sulphuric acid, optionally in the presence of a water-miscible solvent, such as a lower alkanol, for example methanol, a ketone, for example acetone, an ether, for example tetrahydrofurane, or a nitrile, for example acetonitrile. The thio protected groups mentioned can be split off particularly rapidly in the presence of additional reagents, such as sodium thiosulphate, sulphurous acid, thioacetamide, thiourea and potassium iodide.

An amino group protected with an organic silyl or stannyl group, in a resulting compound, can be liberated by treatment with an aqueous or alcoholic agent, for example with a lower alkanol, such as methanol, or a mixture thereof; usually, the splitting of an amino group protected in this way already takes place during working up of the acylation product.

An amino group, present in the form of an azido group, in the aminomethyl substituent of a resulting compound can be converted to the unsubstituted amino group in a manner which is in itself known by means of reduction, for example by treatment with hydrogen in the presence of a hydrogenation catalyst, such as a nickel catalyst or palladium catalyst, for example in the presence of Raney nickel or palladium on charcoal, under mild conditions, for example under atmospheric pressure and/or at room temperature or only slightly elevated temperature, and also by treatment with a phosphine, such as a triarylphosphine, for example triphenylphosphine, or with tin-II chloride.

The reaction products which are formed by the acylation, according to the invention, of compounds of the formula II, wherein the amino group is substituted by a silyl or stannyl group, and in which the organic silyl or stannyl group is still on the amide nitrogen, are customarily converted during working up, especially under hydrolytic and/or alcoholytic conditions, for example such as are customary for the removal of organic silyl or stannyl groups from amino groups, into compounds of the formula I.

The reaction products which are formed by the acylation, according to the invention, of compounds of the formula II, wherein the amino group is substituted by an ylidene group, are also customarily converted during working up, especially by hydrolysis, for example by treatment with water, into compounds of the formula I.

In a compound of the formula I obtainable according to the invention and possessing a protected, especially esterified, carboxyl groups of the formula —C(=O)—$R_o$, the latter can be converted into the free carboxyl group in a manner which is in itself known, for example by solvolysis, treatment with a nucleophilic reagent, irradiation or reduction, that is to say depending on the nature of the group $R_o$. A carboxyl group esterified by a suitable 2-halogeno-lower alkyl group, such as 2,2,2-trichloroethyl or 2-iodoethyl, or by an arylcarbonylmethyl group, such as phenacyl, can be split, for example by treatment with a chemical reducing agent, such as a metal, for example zinc, or a reducing metal salt, such as a chromium-II salt, for example chromium-II acetate, usually in the presence of a hydrogen donor which, together with the metal, is capable of producing nascent hydrogen, such as an acid, above all acetic acid and also formic acid, water preferably being added; a carboxyl group esterified by an arylcarbonyl group, for example a phenacyl group, can also be converted into the free carboxyl group by treatment with a nucleophilic, preferably salt-forming, reagent, such as sodium thiophenolate or sodium iodide. A carboxyl group esterified by a suitably substituted arylmethyl group can be converted into the free carboxyl group, for example by irradiation, preferably with ultraviolet light, for example below 290 m$\mu$, if the arylmethyl group represents, for example, a benzyl radical which is optionally substituted in the 3-, 4- and/or 5-position, for example by lower alkoxy and/or nitro groups, or with ultraviolet light of longer wavelengths, for example above 290 m$\mu$, if the arylmethyl group denotes, for example, a benzyl radical which is substituted in the 2-position by a nitro group. The carboxyl group can be liberated from a carboxyl group esterified with a suitably branched lower alkyl group, for example tert.-butyl, with a suitable cycloalkyl group, such as 1-adamantyl, or with a diphenylmethyl group, for example benzhydryl, for example by treatment with a suitable acid agent, such as formic acid or trifluoroacetic acid, optionally with the addition of a nucleophilic reagent, such as phenol or anisole. An esterified carboxyl group which can be split hydrolytically, such as a carboxyl group esterified by a suitably substituted phenyl radical or a diacyliminomethyl radical, and also a carboxyl group esterified with the 4-hydroxy-3,5-di-tert.-butylbenzyl radical, can be split, depending on the nature of the ester grouping, for example by treatment with an acid or weakly basic aqueous agent, such as hydrochloric acid or aqueous sodium bicarbonate or an aqueous potassium phosphate buffer of pH about 7 to about 9, and an esterified carboxyl group which can be split hydrogenolytically, such as an $\alpha$-aryl-lower alkyl group which is optionally substituted in the aryl radical, for example benzyl, 4-methoxybenzyl or 4-nitrobenzyl, can be split by hydrogenolysis, for example by treatment with hydrogen in the presence of a noble metal catalyst, for example a palladium catalyst.

A carboxyl group protected, for example, by silylation or stannylation, as well as by phosphorylation, can be liberated in the customary manner, for example by hydrolysis or alcoholysis.

The new compounds of the formula I can also be obtained when the methoxy group is introduced into the 6$\alpha$-position or 7$\alpha$-position of a penam compound or 3-cephem compound of the formula

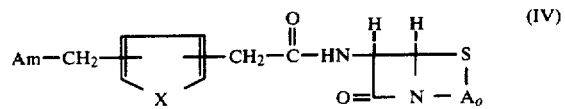

wherein an amino group Am is present, if necessary, in the protected form and the radical of the formula -S-$A_o$- has the abovementioned meaning and a carboxyl group of the formula —C(=O)—$R_o$ is preferably present in the protected form, or of a salt thereof, and, if desired or necessary, the additional process steps are carried out.

The methoxy group can be introduced into the 6$\alpha$-position of a penam starting material of the formula IV or into the 7$\alpha$-position of a 3-cephem starting material of the formula IV in a manner which is in itself known.

Thus, an acylimino compound of the formula

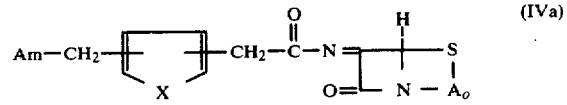

wherein an amino group Am is present, if necessary, in the protected form and the radical of the formula -S-$A_o$- has the abovementioned meaning and a carboxyl group of the formula —C(=O)—$R_o$ is present in the protected form, can be treated with methanol and in a resulting compound a protected amino group Am can be converted into a free amino group Am and, if necessary or desired, a carboxyl group of the formula —C(=O)—$R_o$ can be converted into a carboxyl group of the formula —C(=O)—R and/or, if desired, a group $R_1$ can be converted into another group $R_1$ and/or, if desired, a resulting salt can be converted into the free compound or into another salt, or a resulting free compound can be converted into a salt.

In the starting material of the formula IVa, free functional groups, especially a primary or a secondary amino group Am and a carboxyl group —C(=O)—$R_o$ in a radical -S-A$_o$-, and also free functional groups which may be present in a radical R$_2$, are present in the protected form, for example as indicated above, an amino group Am is present, for example, in the form of a corresponding acylamino group, which preferably can be split easily, and also of a corresponding arylmethylamino group, a 2-carbonyl-1-vinyl-amino group, an arylthioamino group or an aryl-lower alkylthioamino group, a carboxyl group is present, for example, as an esterified carboxyl group, which preferably can be split easily, and a functional group in the radical R$_2$, such as, for example, a hydroxy group, is present as indicated above in the protected form, for example in the form of an acyloxy group.

The above reaction is carried out in a manner which is in itself known, usually in the presence of a solvent or diluent or of a mixture thereof, it being possible for methanol at the same time also to serve as the solvent or diluent, preferably with cooling, for example down to about −80°, as well as at room temperature or with slight warming and, if necessary, in a closed vessel and/or under an inert gas atmosphere, for example a nitrogen atmosphere.

The starting material of the formula IVa is usually reacted in the crude form, that is to say without being isolated after its preparation, with the methanol or is formed in the presence of this reagent. In this reaction, for example, a compound of the formula IV, wherein an amino group Am, if necessary, and the carboxyl group of the formula —C(=O)—R$_o$ as well as any additional functional groups which may be present are in the protected form, is used as the starting material and is treated with an anion-forming agent, followed by a N-halogenating agent, and, if necessary, the resulting product is reacted with a base which splits off hydrogen halide, or a compound of the formula

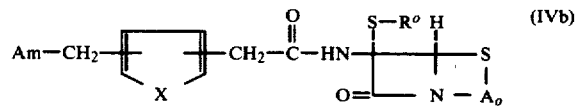

(IVb)

wherein R$^o$ represents an organic radical and wherein an amino group Am, if necessary, and the carboxyl group of the formula —C(=O)—R$_o$ as well as any additional functional groups which may be present are in the protected form, is reacted with halogen, followed by a base. In this way it is possible to obtain, as a product which is usually not isolated, the corresponding 6-acylimino-penam compound of the formula IVa, or 7-acylimino-3-cephem compound of the formula IVa, which is converted, in the presence of methanol, into the desired 6β-acylamino-6α-methyl-penam compound or 7β-acylamino-7α-methoxy-3-cephem compound, on which the abovementioned additional steps are carried out, if necessary or desired.

A suitable anion-forming agent, with which a starting material of the formula IV is reacted, is above all an organometallic base, especially an organo-alkali metal base, above all an organo-lithium base. Such compounds are, in particular, corresponding alcoholates, such as suitable lithium lower alkanolates, above all lithium methylate, or corresponding metal-hydrocarbon bases, especially lithium-lower alkanes and preferably lithiumphenyl. The reaction with the anion-forming organometallic base is usually carried out with cooling, for example at about 0° C. down to about −80° C., and in the presence of a suitable solvent or diluent, for example an ether, such as tetrahydrofurane, also in the presence of methanol when lithium methylate is used, and, if desired, in a closed vessel and/or in an inert gas atmosphere, for example a nitrogen atmosphere.

A sterically hindered, organic hypohalite, especially hydrochlorite, and above all a corresponding aliphatic hypohalite, for example hypochlorite, such as a tert.-lower alkyl hypohalite, for example hypochlorite, is customarily used as the N-halogenating agent. Above all, tert.-butyl hypochlorite is used, which is reacted with the non-isolated product from the anionisation reaction.

The N-halogenated intermediate is converted, in the presence of an excess of the anion-forming base, especially of lithium methylate, under the reaction conditions and without being isolated, into the acylimino compound of the formula IVa and this is converted, in the presence of methanol, directly into the 6α-methoxy-penam compound or 7α-methoxy-3-cephem compound. If necessary, the elements of the hydrogen halide acid, especially of hydrochloric acid, must be split off from the N-halogenated intermediate; this is effected by the addition of a base which splits off hydrogen halide, such as a suitable alkali metal lower alkanolate, for example lithium tert.-butylate, and this reaction usually takes place under the conditions of the anion-forming and N-halogen compound-forming reaction, it being possible to work in the presence of methanol and to obtain direct the 6α-methoxy-penam compound or 7α-methoxy-3-cephem compound in place of the acylimino compound. That is to say, a compound of the formula IV, wherein functional groups are customarily present in the protected form, is used as the starting material and this is reacted with an excess of the anion-forming agent, for example lithium methylate or phenyl lithium, in the presence of methanol, the reaction product is then treated with the N-halogenating agent, for example tert.-butyl hypochlorite and in this way the desired compound of the formula I is obtained direct, it being possible, if necessary or desired, to liberate protected functional groups in this compound of the formula I. However, it is also possible to add the methanol subsequently, in which case the dehydrohalogenation and the addition of methanol can be carried out at somewhat higher temperatures than the anion-forming and N-halogen compound-forming reactions, for example at about 0° C. down to about −20° C., if necessary in a closed vessel and/or in an inert gas atmosphere, for example a nitrogen atmosphere.

In a starting material of the formula IVb, an organic radical R$^o$ above all denotes a hydrocarbon radical of aliphatic character, such as lower alkyl and especially methyl. The reaction with halogen, above all with chlorine, and with a base is customarily carried out in the presence of a suitable solvent or diluent, such as a halogenated hydrocarbon, for example methylene chloride, and with cooling, for example down to about −80° C., and, if necessary, is caarried out in a closed vessel and/or in an inert gas atmosphere, for example a nitrogen atmosphere. A suitable organic base, such as a tertiary amine, for example a tri-lower alkylamine, such as triethylamine, is preferably used as the base and is usually added to the above halogenation mixture together with methanol and under the conditions of the halogenation process. In this way the 6-acylimino-penam starting material of the formula IV, or the 7-acylimino-3-cephem starting material of the formula IV, is converted direct into a 6β-acylamino-6α-methoxy-penam compound of the formula I, or a 7β-acylamino-7α-methoxy-3-cephem compound of the formula I, which compounds can be converted, if necessary or desired, into the desired compound of the formula I.

The methoxy group can also be introduced into the 6α-position of 6β-acylamino-penam compounds, or into the 7α-position of 7β-acylamino-3-cephem compounds, by exchanging an exchangeable group which is present in this position. Thus, a compound of the formula IVb, wherein $R^o$ has the indicated meaning and above all represents an aliphatic hydrocarbon radical, such as lower alkyl and especially methyl, and wherein an amino group Am, if necessary, and the carboxyl group of the formula —C(=O)—$R_o$, as well as any additional functional groups which may be present, are in the protected form, can be reacted with methanol in the presence of a desulphurising agent.

Desulphurising in the presence of methanol is customarily carried out using a suitable silver or mercury compound, such as silver oxide or mercury oxide, or especially a corresponding salt, such as a silver-I salt or mercury-II salt with an organic carboxylic acid, for example a silver-I lower alkanoate or a mercury-II lower alkanoate, especially mercury-II acetate. The reaction is carried out in the presence of a solvent or diluent, for example an ether, such as dimethoxyethane, or of a solvent mixture, it also being possible to use an excess of methanol as the solvent or diluent, with cooling, for example down to about −30° C., at room temperature or with slight warming, for example up to about +70° C., if necessary in a closed vessel and/or in an inert gas atmosphere, for example a nitrogen atmosphere.

In the compounds obtainable according to the variants of the above methoxylation process, which preferably are carried out by the methods described by Koppel and Kocher, J. Am. Chem. Soc., Volume 95, page 2403 (1973), Spitzer and Goodson, Tetrahedron Letters, page 273 (1973), and Slusarchyk et al. J. Org. Chem., Volume 38, page 943 (1973), a protected amino group Am is liberated by the abovementioned processes and, if necessary, a protected carboxyl group of the formula —C(=O)—$R_o$ is converted, by the indicated process, into a carboxyl group of the formula —C(=O)—R; if desired, it is possible, as indicated, in a resulting compound, to convert the carboxyl group of the formula —C(=O)—R into another carboxyl group of the formula —C(=O)—R and/or to convert a group $R_1$ into another group $R_1$.

The compounds of the present invention can also be obtained when, in a compound of the formula

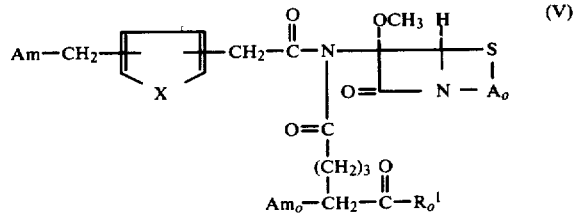

(V)

wherein $Am_o$ represents a protected amino group and $R_o^1$ denotes a radical which, together with the carbonyl grouping of the formula —C(=O)—, forms a preferably protected carboxyl group and wherein an amino group Am, if necessary, is present in a protected form, which differs in the way it is converted into the corresponding free amino group Am from that of the protected amino group $Am_o$, the group $Am_o$ is converted into the free amino group, the 5-amino-5-carboxy-valeryl radical being split off under the reaction conditions, and, in a resulting compound, a protected amino group Am is converted into the corresponding free amino group Am and, if necessary or desired, a carboxyl group of the formula —C(=O)—$R_o$ is converted into a carboxyl group of the formula —C(=O)—R and/or, if desired, a group $R_1$ is converted into another group $R_1$ and/or, if desired, a resulting salt is converted into the free compound or into another salt, or a resulting free compound is converted into a salt.

In the abovementioned starting material, the carboxyl groups of the formula —C(=O)—$R_o$ in the radical of the formula -S-$A_o$-, and the carboxyl groups of the formula —C(=O)—$R_o^1$, usually represent protected carboxyl groups, such as, for example, the abovementioned protected carboxyl groups, it also being possible for a group of the formula —C(=O)—$R_o^1$ to be an esterified carboxyl group which cannot be split, such as, for example, methoxycarbonyl. An amino group Am, above all a secondary amino group Am, is present, as already mentioned, in the protected form; usually functional groups which are present in a radical $R_1$ are also protected, for example as indicated. Groups protected in this way are usually not liberated under the reaction conditions.

A protected amino group $Am_o$ is usually a corresponding amino group which can be converted into the free amino group, preferably under mild conditions. Protective groups are, for example, acyl, arylmethyl, 2-carbonyl-1-vinyl, arylthio, aryl-lower alkylthio or arylsulphonyl groups, which can be split off in different ways.

An easily removable acyl group is, for example, the formyl group or the acyl radical of a half-ester of carbonic acid, such as a lower alkoxycarbonyl group which preferably has multiple aliphatic substituents or branching and/or aromatic or heteroaromatic substituents on the carbon atom in the α-position to the oxy group, or a methoxycarbonyl group which is substituted by an arylcarbonyl radical, especially a benzoyl radical, or a lower alkoxycarbonyl group which is substituted in the β-position by halogen, such as tert.-lower alkoxycarbonyl, for example tert.-butoxycarbonyl or tert.-pentyloxycarbonyl, arylcarbonylmethoxycarbonyl, for example phenacyloxycarbonyl, 2-halogenoethoxycarbonyl, for example 2,2,2-trichloroethoxycarbonyl or 2-iodoethoxycarbonyl, or a group which can be converted into the latter, such as 2-chloroethoxycarbonyl or 2-bromoethoxycarbonyl, and also preferably polycyclic cycloalkoxycarbonyl, for example adamantyloxycarbonyl, phenyl-lower alkoxycarbonyl, especially α-phenyl-lower alkoxycarbonyl, which is optionally substituted, for example by lower alkyl, such as tert.-butyl, hydroxyl, lower alkoxy, such as methoxy, and/or nitro, for example 4-methoxy-benzyloxycarbonyl, 4-hydroxy-3,5-bis-tert.-butylbenzyloxycarbonyl, 4-nitrobenzyloxycarbonyl or α-4-biphenylyl-α-methylethoxycarbonyl, as well as diphenylmethoxycarbonyl which is optionally substituted, for example by lower alkoxy, such as methoxy, for example diphenylmethoxycarbonyl, or furyl-lower alkoxycarbonyl, above all α-furyl-lower alkoxycarbonyl, for example furfuryloxycarbonyl. An acyl group can also be the corresponding radical of a suitable carboxylic acid, such as of an aryldicarboxylic acid, for example the phthaloyl radical, or of a halogeno-lower alkanecarboxylic acid, for example the trifluoroacetyl radical.

Examples of easily removable arylmethyl groups which may be mentioned are optionally substituted polyarylmethyl groups, such as diarylmethyl groups or triarylmethyl groups, for example trityl which is optionally substituted, such as by lower alkoxy, such as methoxy, in particular optionally o- and/or p-methoxy-substituted trityl.

Easily removable 2-carbonyl-1-vinyl groups, which, together with an amino group, form either an enamine or the ketimine tautomeric thereto, are, for example, 2-lower alkoxycarbonyl-1-lower alkylvinyl groups, especially the 2-methoxycarbonyl-1-methyl-1-vinyl group.

Easily removable arylthio or aryl-lower alkylthio groups are, for example, substituted phenylthio groups, for example phenylthio groups substituted by nitro or halogen, for example chlorine, such as the 2-nitrophenylthio group, the 2,4-dinitrophenylthio group or the pentachlorophenylthio group, and also triarylmethylthio groups, for example the triphenylmethylthio group.

An amino group $Am_o$ protected in this way can be converted into the free amino group in a manner which is in itself known; the liberated amino group effects the intramolecular aminolysis, which takes place under the reaction conditions, of the 5-amino-5-carboxy-valeroyl radical, which is split off and is then customarily present in the form of the protected 2-oxo-piperidine-6-carboxylic acid.

A protected amino group $Am_o$ can be split into a free amino group in a manner which is in itself known but which differs depending on the nature of the protective group, especially by solvolysis, treatment with a nucleophilic reagent or reduction.

A formylamino group $Am_o$ can be split, for example, by treatment with an acid agent, for example p-toluenesulphonic acid or hydrochloric acid, with a weakly basic agent, for example dilute ammonia, or with a decarbonylating agent, for example tris-(triphenylphosphine)-rhodium chloride.

An α-polybranched lower alkoxycarbonylamino group, for example tert.-butoxycarbonylamino, and also a polycyclic cycloalkoxycarbonylamino group, for example 1-adamantyloxycarbonylamino, an optionally substituted diphenylmethoxycarbonylamino group, for example diphenylmethoxycarbonylamino, or an α-furyl-lower alkoxycarbonylamino group $Am_o$ can be split, for example, by treatment with a suitable acid, such as a strong, preferably aliphatic, carboxylic acid, such as an optionally halogenated, especially fluorinated, lower alkanecarboxylic acid, above all formic acid or trifluoroacetic acid, optionally in the presence of a nucleophilic reagent, for example anisole, whilst a suitably substituted benzyloxycarbonylamino group, for example 4-hydroxy-3,5-di-tert.-butyl-benzyloxycarbonylamino; can be split preferably by treatment with an optionally anhydrous, weak base, such as an alkali metal salt of an organic carboxylic acid, for example the sodium salt or potassium salt of 2-ethylpentanecarboxylic acid, with an alkali metal salt of a thiophenol, for example the sodium salt of thiophenol, or with a suitable organic amine, for example ethylamine or cyclohexylamine, or a suitably substituted lower alkanoylamino group, for example trifluoroacetylamino, can be split hydrolytically under weakly basic conditions. A 2-halogeno-lower alkoxycarbonylamino group, such as 2,2,2-trichloroethoxycarbonylamino or 2-iodoethoxycarbonylamino (a group which can be converted into 2-iodoethoxycarbonylamino, such as the corresponding 2-chloroethoxycarbonylamino or 2-bromoethoxycarbonylamino, being converted, before removal, into 2-iodoethoxycarbonylamine in a manner which is in itself known, for example by treatment with a suitable iodine salt, such as an alkali metal iodide, such as sodium iodide, in the presence of a solvent, such as acetone), or a phenacyloxycarbonylamino group, such as phenacyloxycarbonylamino, can be split by treatment with a chemical reducing agent, such as a suitable reducing metal or a corresponding metal compound, for example zinc, or a chromium-II compound, such as chromium-II chloride or chromium-II acetate, usually in the presence of an agent which, together with the metal or the metal compound, produces nascent hydrogen, preferably in the presence of aqueous acetic acid.

Furthermore, an amino group $Am_o$ protected by a preferably suitably substituted benzyloxycarbonyl group, such as 4-methoxy- or 4-nitro-benzyloxycarbonylamino, can be split hydrogenolytically, for example by treatment with hydrogen in the presence of a hydrogenation catalyst, for example palladium, or, in particular, 4-nitrobenzyloxycarbonylamino, can be split by treatment with a chemical reducing agent, for example sodium dithionite.

A polyarylmethylamino group $Am_o$, such as tritylamino, can be split, for example, by treatment with an acid agent, such as a mineral acid, for example hydrochloric acid.

An amino group protected in the form of an enamine or of a ketimine tautomeric thereto, as well as the amino groups $Am_o$ protected by arylthio, aryl-lower alkylthio and arylsulphonyl, which have been mentioned, can be split, for example, by treatment with an acid agent, above all an aqueous acid, such as an organic caboxylic acid, for example formic acid, acetic acid or propionic acid, or a mineral acid, for example hydrochloric acid or sulphuric acid, optionally in the presence of a water-miscible solvent, such as a lower alkanol, for example methanol, a ketone, for example acetone, an ether, for example tetrahydrofurane, or a nitrile, for example acetonitrile. The thio-protective groups mentioned can be split off particularly rapidly in the presence of additional reagents, such as sodium thiosulphate, sulphurous acid, thioacetamide, thiourea and potassium iodide.

The splitting reactions described above are carried out under conditions which are in themselves known, if necessary with cooling or warming, in a closed vessel and/or in an inert gas atmosphere, for example a nitrogen atmosphere.

As mentioned above, simultaneous liberation of other protected functional groups present in the starting material should not take place under the reaction conditions. Thus, for example, the protected amino group $Am_o$ can be an amino group which can be split on treatment with a chemical reducing agent, for example with zinc in the presence of aqueous acetic acid, for example a 2-halogeno-lower alkoxycarbonylamino group which can be split under these conditions, such as 2,2,2-trichloroethoxycarbonylamino, whilst an amino group Am can be protected by a lower alkoxycarbonyl group which can be split off on treatment with a suitable acid, such as trifluoroacetic acid, for example by an α-polybranched lower alkoxycarbonyl group, such as tert.-butoxycarbonyl, and a carboxyl group of the formula —C(=O)—R$_o$, and also a free carboxyl group which may be present in a group R$_2$ in the radical of the formula -S-A$_o$-, can be protected by a diphenylmethyl group which can also be split off on treatment with a suitable acid, such as trifluoroacetic acid, for example by an optionally substituted diphenylmethyl group, for example benzhydryl; in the protected form the latter groups withstand the above-mentioned reductive splitting conditions and, if necessary or desired, are liberated only after intramolecular aminolysis of a 5l -amino-5-carboxy-valeryl radical has taken place.

The above process can be carried out, for example, according to the method described by Sletzinger et al. J. Am. Chem. Soc., Volume 94, page 1410 (1972).

The compounds of the present invention can also be manufactured when a compound of the formula

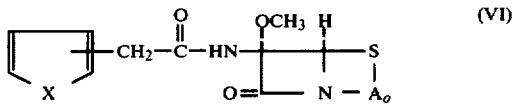

wherein the radical of the formula -S-A$_o$- has the above-mentioned meaning and a carboxyl group of the formula —C(=O)—R$_o$ is preferably present in the protected form, is reacted with a compound of the formula Am-H (VII), an additional hydrogen atom in an amino group Am which is unsubstituted or monosubstituted by optionally substituted lower alkyl being replaced by an amino protective group, and with formaldehyde in the presence of a strong, at most slightly nucleophilic, acid, and, in a resulting compound, a protected amino group Am is converted into a free amino group Am and, if necessary or desired, a carboxyl group of the formula —C(=O)—R$_o$ is converted into a carboxyl group of the formula —C(=O)—R and/or, if desired, a group R$_1$ is converted into another group R$_1$ and/or, if desired, a resulting salt is converted into the free compound or into another salt, or a resulting free compound is converted into a salt.

An unsubstituted or monosubstituted amino group present in the protected form in the starting material of the formula VII contains, as the amino protective group, one of the abovementioned amino protective groups, for example the amino protective groups which were mentioned in connection with an amino group Am and which cannot be split off under the reaction conditions, that is to say in the presence of the strong, at most slightly nucleophilic, acid. Such an amino protective group is, above all, a corresponding acyl group, such as formyl or suitable, optionally substituted, lower alkanoyl, especially trifluoroacetyl, and above all suitably etherified hydroxycarbonyl, which can be split off, for example, under reductive conditions, on treatment with a nucleophilic reagent or on irradiation, above all 2-halogeno-lower alkoxycarbonyl, for example 2,2,2-trichloroethoxycarbonyl, 2-chloroethoxycarbonyl, 2-bromoethoxycarbonyl or 2-iodoethoxycarbonyl, arylcarbonylmethoxycarbonyl, for example phenacyloxycarbonyl, or α-aryllower alkoxycarbonyl, such as α-phenyl-lower alkoxycarbonyl which is optionally substituted, for example by lower alkoxy, such as methoxy, and/or nitro, for example benzyloxycarbonyl, 4-methoxy-benzyloxycarbonyl, 4-nitrobenzyloxycarbonyl or 4,5-dimethoxy-2-nitrobenzyloxycarbonyl.

Formaldehyde can be used as such or in the form of a reactive derivative thereof, above all in the form of a polymer, such as paraformaldehyde.

Strong, at most slightly nucleophilic, acids are, above all, strong organic carboxylic acids, such as preferably halogen-substituted lower alkanecarboxylic acids, for example formic acid (optionally in the presence of a strong organic sulphonic acid, such as a strong arylsulphonic acid, for example 4-methylbenzenesulphonic acid) and above all trifluoroacetic acid.

The above reaction is customarily carried out by treating a reaction mixture of a compound of the formula VII with the formaldehyde or a derivative thereof (which is prepared, for example, in the presence of an inert solvent and a weakly basic agent, such as an alkali metal carbonate, for example potassium carbonate, and, if necessary, with removal of water and with formation of a compound of the formula R$_x$-NH-CH$_2$-OH (VIIa), which is obtainable as an intermediate), with the starting material of the formula VI and with the strong, at most slightly nucleophilic, acid and working in the presence of an inert solvent or solvent mixture, the stirring or warming and/or in an inert gas atmosphere.

In a compound of the formula I, obtainable by this process, an amino group Am is optionally present in the protected form, amino protective groups being, above all, the abovementioned acyl radicals. They are split off in a manner which is in itself known, for example as described above, a formyl group being split off, for example, by treatment with a strong acid, for example hydrochloric acid or 4-methylphenylsulphonic acid, a trifluoroacetyl group being split off, for example, hydrolytically under weakly basic conditions, a suitable 2-halogeno-lower alkoxycarbonyl group or arylcarbonylmethoxycarbonyl group being split off, for example, by treatment with a chemical reducing agent, such as a suitable reducing metal or a corresponding metal compound, for example zinc, or a chromium-II compound, such as chromium-II chloride or chromium-II acetate, usually in the presence of an agent which, together with the metal or the metal compound, produces nascent hydrogen, preferably in the presence of aqueous acetic acid, an arylcarbonylmethoxycarbonyl group also being split off by treatment with a suitable nucleophilic, preferably salt-forming, reagent, such as sodium thiophenolate, and an α-aryl-lower alkoxycarbonyl group being split off hydrogenolytically, for example by treatment with hydrogen in the presence of a hydrogenation catalyst, for example palladium, or, such as 4-nitrobenzyloxycarbonyl, by treatment with a chemical reducing agent, for example sodium dithionite.

The compounds of the formula (I), wherein R$_a$ and R$_b$ are different from hydrogen, can also be manufactured when, in a compound of the formula

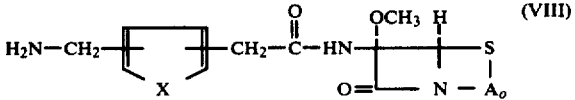

or in a salt thereof, the free amino group H$_2$N— is converted into a substituted amino group Am and, if desired or necessary, the additional process steps are carried out.

The substitution of the free amino group in a starting material of the formula VIII is carried out in a manner which is in itself known, for example by treatment with a reactive ester of an alcohol of the formula $R_a$—OH (IXa) or $R_b$—OH (IXb) or of a diol of the formula HO—$(R_a+R_b)$—OH (IXc). Such reactive esters are, in particular, esters with strong inorganic acids, especially mineral acids, or with strong organic acids, especially corresponding organic sulphonic acids. Esters of this type are corresponding halides, for example chlorides or bromides, as well as sulphates or bisulphates, or corresponding lower alkylsulphonyloxy compounds, for example methylsulphonyloxy compounds or arylsulphonyloxy compounds, for example 4-methylphenylsulphonyloxy compounds. The reaction with such reagents is carried out, if necessary, in the presence of a condensing agent, such as an alkali metal bicarbonate or a suitable organic base, such basic condensing agents preferably being used in at most slight excess. The substitution of the free amino group in a starting material of the formula VIII can also be effected by reaction with an optionally substituted lower alkanal or lower alkanone, with simultaneous or subsequent treatment with a reducing agent. A suitable reducing agent is, above all, catalytically activated hydrogen, a noble metal catalyst, such as a palladium or platinum catalyst preferably being used as the catalyst. When formaldehyde is used as the lower alkanal, the reducing agent is, above all, formic acid.

The above substitution reactions are usually carried out in the presence of a solvent or diluent, it also being possible to employ reactants as the solvent or diluent, and, if necessary, with cooling or warming, in a closed vessel and/or in an inert gas atmosphere.

The 3-cephem compounds of the present invention can also be obtained when a 2-cephem compound of the formula

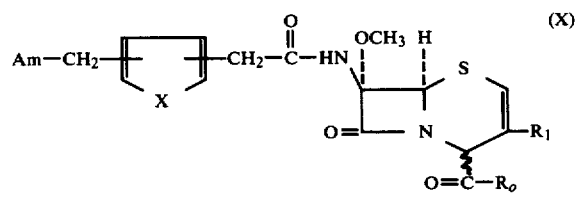

wherein an amino group Am and/or a carboxyl group of the formula —C(=O)—$R_o$, if necessary or desired, is present in the protected form, is isomerised to give a 3-cephem compound and, if desired or necessary, the additional process steps are carried out.

The isomerisation of a 2-cephem compound into the corresponding 3-cephem compound can be carried out in a manner which is in itself known.

Thus, a 2-cephem compound of the formula X can be isomerised by treating it with a weakly basic agent and isolating the corresponding 3-cephem compound from an equilibrium mixture which may be obtained.

Examples of suitable isomerising agents are organic nitrogen-containing bases, such as tertiary heterocyclic bases of aromatic character, and above all tertiary aliphatic, azacycloaliphatic or araliphatic bases, such as N,N,N-tri-lower alkylamines, for example N,N,N-trimethylamine, N,N-dimethyl-N-ethylamine, N,N,N-triethylamine or N,N-diisopropyl-N-ethylamine, N-lower alkyl-azacycloalkanes for example N-methyl-piperidine, or N-phenyl-lower alkyl-N,N-di-lower alkylamines, for example N-benzyl-N,N-dimethylamine, as well as mixtures thereof, such as the mixture of a base of the pyridine type, for example pyridine, and a N,N,N-tri-lower alkylamine, for example pyridine and triethylamine. Furthermore, it is also possible to use inorganic or organic salts of bases, especially of medium strength to strong bases, with weak acids, such as alkali metal salts or ammonium salts of lower alkanecarboxylic acids, for example sodium acetate, triethylammonium acetate or N-methyl-piperidine acetate, as well as other analogous bases or mixtures of such basic agents.

The above isomerisation with basic agents can be carried out, for example, in the presence of a derivative of a carboxylic acid which is suitable for forming a mixed anhydride, such as a carboxylic acid anhydride or carboxylic acid halide, for example with pyridine in the presence of acetic anhydride. This reaction is preferably carried out in an anhydrous medium, in the presence or absence of a solvent, such as an optionally halogenated, for example chlorinated, aliphatic, cycloaliphatic or aromatic hydrocarbon, or of a solvent mixture, it being possible for bases which are used as reactants and are liquid under the reaction conditions at the same time also to serve as solvents, if necessary with cooling or heating, preferably in a temperature range from about $-30°$ C. to about $+100°$ C., in an inert gas atmosphere, for example a nitrogen atmosphere, and/or in a closed vessel.

3-Cephem compounds which are thus obtainable can be separated from any 2-cephem compounds of the formula X which may still be present, in a manner which is in itself known, for example by adsorption and/or crystallisation.

The isomerisation of 2-cephem compounds of the formula X can also be carried out by oxidising these in the 1-position, if desired separating an isomer mixture of the 1-oxides of corresponding 3-cephem compounds, which is obtainable, and reducing the 1-oxides of the corresponding 3-cephem compounds, which are thus obtainable.

Suitable oxidising agents which can be used for the oxidation of 2-cephem compounds in the 1-position are inorganic per-acids which have a reduction potential of at least $+1.5$ volt and which consist of non-metallic elements, organic per-acids or mixtures of hydrogen peroxide and acids, especially organic carboxylic acids, having a dissociation constant of at least $10^{-5}$. Suitable inorganic per-acids are periodic acid and persulphuric acid. Organic per-acids are appropriate percarboxylic acids and persulphonic acids, which can be added as such or can be formed in situ by the use of at least one equivalent of hydrogen peroxide and of a carboxylic acid. It is appropriate to use a large excess of the carboxylic acid when, for example, acetic acid is used as the solvent. Suitable per-acids are, for example, performic acid, peracetic acid, pertrifluoroacetic acid, permaleic acid, perbenzoic acid, monoperphthalic acid or p-toluenepersulphonic acid.

The oxidation can also be carried out using hydrogen peroxide with catalytic amounts of an acid having a dissociation constant of at least $10^{-5}$, it being possible to employ low concentrations, for example 1–2% and less, but also larger amounts, of the acid. The activity of the mixture depends above all on the strength of the acid. Examples of suitable mixtures are those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid having a dissociation constant of at least $10^{-5}$, its activity depending on its strength. Acids suitable as catalysts are, for example, acetic acid, perchloric acid and trifluoroacetic acid. Usually, at least equimolar amounts of the oxidising agent, and preferably a small excess of about 10% to about 20% are used. The oxidation is carried out under mild conditions, for example at temperatures from about $-50°$ C. to about $+100°$ C., preferably from about $-10°$ C. to about $+40°$ C.

The oxidation of 2-cephem compounds to the 1-oxides of the corresponding 3-cephem compounds can also be carried out by treatment with ozone, as well as with organic hypohalite compounds, such as lower alkyl hypochlorites, for example tert.-butyl hypochlorite, which are used in the presence of inert solvents, such as optionally halogenated hydrocarbons, for example methylene chloride, and at temperatures from about $-10°$ C. to about $+30°$ C., with periodate compounds, such as alkali metal periodates, for example potassium periodate, which are preferably used in an aqueous medium at a pH value of about 6 and at temperatures from about $-10°$ C. to about $+30°$ C., with iodobenzene dichloride, which is used in an aqueous medium, preferably in the presence of an organic base, for example pyridine, and with cooling, for example at temperatures from about $-20°$ C. to about $0°$, or with any other oxidising agent which is suitable for conversion of a thio grouping into a sulphoxide grouping.

In the 1-oxides of 3-cephem compounds, thus obtainable, the additional process steps mentioned in connection with the isomerisation process can be carried out, if desired. Furthermore, a mixture of isomeric α- and β-1-oxides can be separated, for example chromatographically.

The reduction of the 1-oxides of 3-cephem compounds can be carried out in a manner which is in itself known, by treatment with a reducing agent, if necessary in the presence of an activating agent. Possible reducing agents are: catalytically activated hydrogen, using noble metal catalysts which contain palladium, platinum or rhodium and which are optionally employed together with a suitable support, such as charcoal or barium sulphate; reducing tin, iron, copper or manganese cations, which are used in the form of appropriate compounds or complexes of inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediaminetetraacetic acid or nitrilotriacetic acid; reducing dithionite, iodide or ferrocyanide anions, which are used in the form of appropriate inorganic or organic salts, such as alkali metal dithionite, iodide or ferrocyanide, for example sodium dithionite or otassium dithionite, sodium iodide or potassium iodide or sodium ferrocyanide or potassium ferrocyanide, or in the form of the corresponding acids, such as hydriodic acid; reducing trivalent inorganic or organic phosphorus compounds, such as phosphines, and also esters, amides and halides of phosphinous, phosphonous or phosphorous acid as well as phosphorus-sulphur compounds corresponding to these phosphorus-oxygen compounds, in which compounds organic radicals above all represent aliphatic, aromatic or araliphatic radicals, for example optionally substituted lower alkyl, phenyl or phenyl-lower alkyl groups, such as, for example, triphenylphosphine, tri-n-butylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide and the like; reducing halogenosilane compounds which possess at least one hydrogen atom bonded to the silicon atom and which, in addition to halogen, such as chlorine, bromine or iodine, can also possess organic radicals, such as aliphatic or aromatic groups, for example optionally substituted lower alkyl or phenyl groups, such as chlorosilane, bromosilane, di- or tri-chlorosilane, di- or tri-bromosilane, diphenylchlorosilane, dimethylchlorosilane and the like; reducing quaternary chloromethyleneiminium salts, especially the chlorides or bromides, wherein the iminium group is substituted by one divalent or by two monovalent organic radicals, such as optionally substituted lower alkylene or lower alkyl groups, such as N-chloromethylene-N,N-diethyliminium chloride or N-chloromethylene-pyrrolidinium chloride; and complex metal hydrides, such as sodium borohydride, in the presence of suitable activating agents, such as cobalt-II chloride, as well as borane dichloride.

As activating agents which are used together with those of the abovementioned reducing agents which do not themselves possess Lewis acid properties, that is to say which are above all employed together with the dithionite, iodide or ferrocyanide reducing agents and the trivalent phosphorus reducing agents which do not contain halogen, or in the catalytic reduction, there should be mentioned in particular organic carboxylic acid halides and sulphonic acid halides, as well as sulphur halides, phosphorus halides or silicon halides having a second order hydrolysis constant equal to or greater than that of benzoyl chloride, for example phosgene, oxalyl chloride, acetic acid chloride or acetic acid bromide, chloroacetic acid chloride, pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethylchlorosilane or trichlorosilane, and also suitable acid anhydrides, such as trifluoroacetic anhydride, or cyclic sultones, such as ethanesultone, 1,3-propanesultone, 1,4-butanesultone or 1,3-hexanesultone.

The reduction is preferably carried out in the presence of solvents or mixtures thereof, the choice of which is above all determined by the solubility of the starting materials and the choice of the reducing agent, thus, for example, lower alkanecarboxylic acids or esters thereof, such as acetic acid and ethyl acetate, are used in the case of the catalytic reduction and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide or hexamethylphosphoramide, ethers, for example ether, tetrahydrofurane or dioxane, ketones, for example acetone, or sulphones, especially aliphatic sulphones, for example dimethylsulphone or tetramethylene sulphone, and the like are used together with the chemical reducing agents, these solvents preferably not containing any water. The reaction is usually carried out at temperatures from about −20° C. to about 100° C., it being possible to carry out the reaction at lower temperatures if very reactive activating agents are used.

In a compound of the formula I, obtainable according to the invention, which contains a free carboxyl group of the formula —C(=O)—R and in which an amino group Am is optionally present in the protected form, the free carboxyl group can be converted in a manner which is in itself known into an esterified carboxyl group which can be split under physiological conditions. Thus, for example, in a compound of the formula I having a free carboxyl group, or in a salt thereof, for example in an alkali metal salt, such as the sodium salt or potassium salt, or in an alkaline earth metal salt, such as the calcium salt or magnesium salt, or in an optionally substituted ammonium salt, such as the triethylammonium salt, thereof, the carboxyl group can be converted, by reaction with a suitable halide, for example chloride or bromide, into the corresponding esterified carboxyl group —C(=O)—R.

In a compound of the formula I, obtainable according to the invention, wherein Am represents a monosubstituted amino group, such a group can be converted into a corresponding disubstituted tertiary amino group in a manner which is in itself known, for example as described above, by treatment with a reactive ester of an optionally substituted lower alkanol or with an optionally substituted lower alkanal or lower alkanone in the presence of a reducing agent. Furthermore, a substituent, above all a methyl group, can be split off from a disubstituted amino group Am, especially from a corresponding disubstituted amino group Am which contains a methyl group, in a manner which is in itself known, for example by treatment with a halogenoformic acid lower alkyl ester, for example ethyl chloroformate, or with a cyanogen halide, for example cyanogen bromide, and removal of a lower alkoxy carbonyl or cyano group, introduced in this way, under acid conditions, for example by treatment with hydrobromic acid in the presence of formic acid, or with hydrochloric acid.

Furthermore, in a compound of the formula I, obtainable according to the invention, wherein an amino group Am is protected if necessary and wherein the grouping of the formula —S-A—corresponds to a radical of the formula Ib, it is possible, in a manner which is in itself known, to replace a group $R_1$ by another radical $R_1$ or to convert a group $R_1$ into another radical $R_1$.

Thus, for example, it is possible, in a compound of the formula I having a radical of the formula Ib as the grouping of the formula —S-A—, wherein $R_1$ denotes a group of the formula —CH$_2$—R$_2$, and $R_2$ represents, for example, a radical which can be replaced by nucleophilic substituents, or in a salt thereof, to replace such a radical $R_2$ by an etherified or esterified mercapto group $R_2$ by treatment with a mercaptan compound or with a thiol-carboxylic acid compound. A suitable radical which can be replaced by an etherified mercapto group is, for example, an esterified hydroxyl group, for example a hydroxyl group esterified by a hydrogen halide acid, such as hydrochloric acid or hydrobromic acid, or preferably by an organic carboxylic acid, such as an aliphatic (including formic acid), cycloaliphatic, cycloaliphatic-aliphatic, aromatic, araliphatic, heterocyclic or heterocyclic-aliphatic carboxylic acid, and also by a carbonic acid half-derivative, such as a carbonic acid half-ester. Such esterified hydroxyl groups are, for example, lower alkanoyloxy which is optionally substituted, for example by halogen, such as fluorine or chlorine, especially acetoxy as well as halogeno-lower alkanoyloxy, such as halogenoacetoxy, for example trifluoroacetoxy, as well as dichloroacetoxy, and also formyloxy, or optionally substituted benzoyloxy, such as 4-chlorobenzoyloxy.

The reaction of such a compound with a suitable mercaptan compound can be carried out under neutral or weakly basic conditions in the presence of water and optionally of a water-miscible organic solvent. The basic conditions can be set up, for example, by adding an inorganic base, such as an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate. Organic solvents which can be used are, for example, water-miscible alcohols, for example lower alkanols, such as methanol or ethanol, ketones, for example lower alkanones, such as acetone, amides, such as lower alkanecarboxylic acid amides, such as dimethylformamide, and the like.

Esterified hydroxyl groups $R_2$ in a compound of the formula I, wherein the group —S-A— represents the partial formula Ib and $R_1$ denotes the group —CH$_2$—R$_2$, in which $R_2$ represents a hydroxyl group esterified by the acyl radical of an optionally substituted half-amide of carbonic acid, can be introduced, for example, by reacting a corresponding compound of the formula I, wherein $R_2$ represents free hydroxyl (which can be liberated, for example, by splitting off the acetyl radical from an acetoxy group $R_2$, for example by hydrolysis in a weakly basic medium, such as with an aqueous sodium hydroxide solution at pH 9–10, or by treatment with a suitable esterase, such as an appropriate enzyme from *Rhizobium tritolii, Rhizobium lupinii, Rhizobium japonicum* or *Bacillus subtilis,* or a suitable citrus esterase, for example from orange peel), with a suitable carbonic acid derivative, especially with an isocyanate compound or a carbamic acid compound, such as a silyl isocyanate, for example silyl tetraisocyanate, a sulphonyl isocyanate, for example chlorosulphonyl isocyanate, or a carbamic acid halide, for example carbamic acid chloride (which lead to N-unsubstituted 3-aminocarbonyloxymethyl compounds), or with a N-substituted isocyanate compound or with a N-monosubstituted or N,N-disubstituted carbamic acid compound, such as a corresponding carbamic acid halide, for example carbamic acid chloride, the reaction usually being carried out in the presence of a solvent or diluent and, if necessary, with cooling or warming, in a closed vessel and/or in an inert gas atmosphere, for example a nitrogen atmosphere.

Furthermore, a compound of the formula I, wherein the grouping —S-A— corresponds to a radical of the formula Ib, in which $R_2$ represents, for example, the radical defined above, which can be replaced by nucleophilic substitution, can be reacted with a tertiary organic base, especially an optionally substituted pyridine, under neutral or weakly acid conditions, preferably at a pH value of about 6.5, in the presence of water and optionally in a water-miscible organic solvent and compounds of the formula I, wherein the grouping of the formula —S-A— denotes a radical of the formula Ib, wherein $R_1$ represents the radical of the formula —CH$_2$—R$_2$ and $R_2$ represents a quaternary ammonium group, can thus be obtained. The weakly acid conditions can be set up by adding a suitable organic or inorganic acid, for example acetic acid, hydrochloric acid, phosphoric acid or sulphuric acid. Organic solvents which can be used are, for example, the abovementioned water-miscible solvents. In order to increase the yield, certain salts can be added to the reaction mixture, for example alkali metal salts, such as sodium salts and especially potassium salts, of inorganic acids, such as hydrogen halide acids, for example hydrochloric acid and especially hydriodic acid, as well as of thiocyanic acid, or of organic acids, such as lower alkanecarboxylic acids, for example acetic acid. Representative of such salts are, for example, potassium iodide and potassium thiocyanate. Salts of suitable anion exchangers, for example liquid ion exchangers in the form of a salt, such as, for example, Amberlite LA-1 (liquid secondary amines with a molecular weight of 351–393; soluble in oil and insoluble in water; meq/g=2.5–2.7, for example in the form of the acetate), with acids, for example acetic acid, can also be used for this purpose.

Quaternary ammonium groups $R_2$ can be introduced advantageously using an intermediate product of the formula I, in which $R_2$ of the radical $R_1$ in a partial formula Ib represents a substituted carbonylthio group, especially a carbonylthio group with an aromatic substituent, and above all represents the benzoylthio group. An intermediate product of this type, which can be obtained, for example, by reacting a compound of the formula I, wherein —S—A— represents the partial formula Ib, wherein $R_2$ in the radical $R_1$ denotes an esterified hydroxyl group and above all an acyloxy group, especially a lower alkanoyloxy group, for example an acetoxy group, with a suitable salt, such as an alkali metal salt, for example the sodium salt, of a thiocarboxylic acid, such as an aromatic thiocarboxylic acid, for example thiobenzoic acid, is reacted with the tertiary amine, especially a tertiary heterocyclic base, such as an optionally substituted pyridine, whereupon the quaternary ammonium compound is obtained. The reaction is usually carried out in the presence of a suitable desulphurising agent, especially a mercury salt, for example mercury-II perchlorate, and of a suitable solvent or diluent, or of a mixture, if necessary with cooling or warming, in a closed vessel and/or in an inert gas atmosphere, for example a nitrogen atmosphere.

Salts of compounds of the formula I can be manufactured in a manner which is in itself known. Thus, salts of compounds of the formula I having acid groups can be formed, for example, by treatment with metal compounds, such as alkali metal salts of suitable carboxylic acids, for example the sodium salt of α-ethyl-caproic acid, or with ammonia or a suitable organic amine, preferably using stoichiometric amounts or only a small excess of the salt-forming agent. Acid addition salts of compounds of the formula I are obtained in the customary manner, for example by treatment with an acid or with a suitable anion exchange reagent. Inner salts of compounds of the formula I, which contain a free carboxyl group, can be formed, for example, by neutralising salts, such as acid addition salts, to the isoelectric point, for example using weak bases, or by treatment with liquid ion exchangers.

Salts can be converted into the free compounds in the customary manner, metal salts and ammonium salts, for example, by treatment with suitable acids, and acid addition salts, for example, by treatment with a suitable basic agent.

The process also encompasses those embodiments according to which compounds arising as intermediate products are used as starting materials and the remaining process steps are carried out with these, or the process is discontinued at any stage; furthermore, starting materials can be used in the form of derivatives or can be formed during the reaction.

Preferably, the starting materials used and the reaction conditions chosen are such that the compounds mentioned above as being particularly preferred are obtained.

Starting materials of the formula II, wherein the amino group is optionally substituted by a group which permits acylation, are known or can be manufactured according to known methods.

Thus, compounds of the formula II can be obtained when, in corresponding compounds of the formula

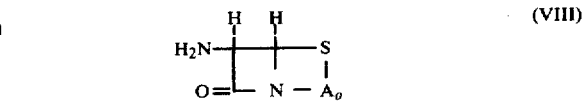

the amino group is converted into the diazo group, for example by treatment with a suitable diazotising agent, especially with nitrous acid or with nitrogen tetroxide, the diazo compound is treated with a halogen azide, for example bromine azide, and the 6-azido-6-halogenopenam compound or 7-azido-7-halogeno-3-cephem compound, thus obtainable, wherein halogen above all represents bromine and which may be present in the form of the 6- or 7-epimer mixture, is reacted with a suitable silver salt, such as silver-I tetrafluoborate, in the presence of methanol. The 6β-azido-6α-methoxypenam compound or 7β-azido-7α-methoxy-3-cephem compound is thus obtained, in which the azido group is converted into the amino group by reduction, for example by catalytic hydrogenation in the presence of a noble metal catalyst, such as platinum oxide or palladium-on-charcoal, and, if necessary, of an activating agent, such as a cobalt salt, for example cobalt-II acetate. This reaction sequence is described, inter alia, for example by Cama et al. J. Am. Chem. Soc., Volume 94, page 1408 (1972).

In a resulting starting material of the formula II, the free amino group can be converted into a substituted amino group which permits acylation, for example by silylation or stannylation, such as by treatment with a suitably substituted silyl halide, for example trimethylsilyl chloride, or by treatment with an aldehyde, especially with an arylcarboxaldehyde, for example an optionally substituted benzaldehyde.

Starting materials of the formula III are known or can be manufactured according to methods which are in themselves known. Thus, for example, the 5-Am-methyl-2-thienyl-acetic acid compounds or 5-Am-methyl-2-furyl-acetic acid compounds can be obtained when a corresponding Am-methylthiophene or Am-methylfurane, wherein an amino group Am is protected, if necessary, for example by one of the protective groups mentioned, or an acid addition salt thereof, such as the hydrochloride, is acetylated by treatment with a suitable acetylating agent, for example with an acetic anhydride, including an acetyl halide, such as acetyl chloride, or preferably with acetic anhydride, in the presence of a suitable catalyst, such as a Lewis acid, for example aluminium chloride or aluminium bromide, or an acid, such as polyphosphoric acid, or preferably trifluoroacetic acid, as well as the anhydride thereof. The reaction can be carried out in an anhydrous solvent, such as an aromatic hydrocarbon, for example benzene, or an excess of the liquid reagents employed, for example an excess of trifluoroacetic acid or acetic acid and/or the anhydrides thereof. When trifluoroacetic acid or trifluoroacetic anhydride is used, a free amino group can be acylated at the same time by the trifluoroacetyl radical.

An acetylated Am-methylthiophene or Am-methylfurane compound, wherein an amino group Am is protected if necessary, for example by the trifluoroacetyl radical, can be converted into a compound of the formula (III), for example according to the method of Willgerodt or Willgerodt-Kindler, for example by heating with ammonium polysulphide or with a primary or secondary amine, such as morpholine, and subsequently hydrolysing the thioamide formed as an intermediate.

On the other hand, an acetylated Am-methyl-thiophene compound or Am-methyl-furane compound, especially such a compound wherein an amino group Am is protected, if necessary, in the indicated manner, for example by the trifluoroacetyl radical, can be converted, by warming with thallium-(III) nitrate in the presence of a lower alkanol, especially methanol, and an acid, for example perchloric acid, into a lower alkyl ester, for example the methyl ester, of an acid of the formula III, from which the free acid can be prepared by hydrolysis.

When a thioamide obtained according to Willgerodt or Willgerodt-Kindler or an ester obtained by the thallium-(III) nitrate method is hydrolysed, an amino protected group which may be present can, depending on the hydrolysis conditions and on the nature of the protective group, also be split off or, if desired, converted. The complete hydrolysis to give a compound of the formula III and an optional subsequent introduction of an amino protective group can also be carried out in one step. For example, a resulting methyl ester of a compound of the formula III, wherein an amino group Am is acylated if necessary, for example with the trifluoroacetyl group, can first be hydrolysed by treatment with a base, for example an alkali metal hydroxide, such as sodium hydroxide, in water or water together with a water-miscible organic solvent, such as dioxane, and, if desired or necessary, can then be treated in the same reaction mixture, for example with tert.-butoxycarbonyl azide, after which, after acidification and customary working up, the desired thiophene-acetic acid or furane-acetic acid having an Am-methyl group protected by tert.-butoxycarbonyl can be obtained.

Furthermore, for example, 4-Am-methyl-2-thienyl-acetic acid compounds or 4-Am-methyl-2-furyl-acetic acid compounds can be obtained when 2-acetyl-thiophene or 2-acetyl-furane is halogeno-methylated, especially chloromethylated, for example by treatment with formaldehyde or a derivative thereof, such as paraformaldehyde, in the presence of a hydrogen halide acid, such as hydrochloric acid, and, in the 2-acetyl-4-halogenomethyl-thiophene compound or 2-acetyl-4-halogenomethyl-furane compound, thus obtainable, wherein halogen above all denotes chlorine, halogen is converted into an amino group Am in a manner which is in itself known, for example by treatment with an amine of the formula Am-H (XI), and the acetyl substituent is then converted into the desired carboxymethyl radical, for example by the process described above.

In a compound of the formula III having an unprotected amino group Am, the latter can, if necessary, be converted by any known method into one of the protected amino groups Am which have been mentioned. Thus, it is possible to introduce an acyl radical as an amino protective group into a primary or secondary amino group Am, for example by the acylation process described above, and also by treatment with a carbonic acid halide compound or carbonic acid azide compound, such as tert.-butoxycarbonyl azide. Furthermore, a secondary amino group Am can be substituted by a di- or tri-arylmethyl group, for example by treatment with a reactive ester of a di- or tri-arylmethanol, such as trityl chloride, preferably in the presence of a basic agent, such as pyridine.

An amino group Am can also be protected by introducing a silyl group and stannyl group. Such groups are introduced in a manner which is in itself known, for example by treatment with a suitable silylating agent, such as a di-halogeno-di-lower alkylsilane or tri-lower alkylsilyl halide, for example dichlorodimethylsilane or trimethylsilyl chloride, or an optionally N-mono-lower alkylated, N,N-di-lower alkylated, N-tri-lower alkylsilylated or N-lower alkyl-N-tri-lower alkylsilylated N-(tri-lower alkyl-silyl)-amine (see, for example, British Pat. No. 1,073,530), or with a suitable stannylating agent, such as a bis-(tri-lower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compound, a tetra-lower alkoxy-tin compound or a tetra-lower alkyl-tin compound as well as a tri-lower alkyl-tin halide, for example tri-n-butyl-tin chloride (see, for example, Netherlands Published Specification No. 67/11,107).

An amino group Am can also be protected by introducing a 2-carbonyl-1-vinyl group, enamine compounds being formed. Such groups can be obtained, for example, by treating the amine with a 1,3-dicarbonyl compound, for example with acetoacetic acid methyl ester or acetoacetic acid N,N-dimethylamide, in an anhydrous medium, for example a lower alkanol, such as methanol.

Arylthio or aryl-lower alkylthio and also arylsulphonyl protective groups can be introduced into suitable amino groups Am by treatment with a corresponding arylthio, aryl-lower alkylthio or arylsulphonyl halide, for example an arylthio, aryl-lower alkylthio or arylsulphonyl chloride.

The reactive functional acid derivatives of an acid of the formula III can be manufactured in a manner which is in itself known. Acid halides are obtained, for example, by reacting a compound of the formula III, if necessary having a protected amino group, or a salt thereof, with a halogenating agent, for example with an acid halide, such as an acid fluoride or acid chloride, of an inorganic acid containing phosphorus or sulphur, for example phosphorus pentachloride, thionyl chloride or oxalyl chloride. The reaction is preferably carried out in a non-aqueous solvent or solvent mixture, such as a carboxylic acid amide, for example dimethylformamide. The resulting acid halide does not need to be further purified but can be reacted direct with the starting material of the formula II, it being possible to use, for example, the same solvents or solvent mixtures as are employed in the manufacture of the acid halide.

Symmetrical anhydrides, or mixed anhydrides which differ from halides, of compounds of the formula III, if necessary having a protected amino group, can be prepared, for example, by reacting a corresponding compound having a free carboxyl group, or preferably a salt, especially an alkali metal salt, for example a sodium salt or ammonium salt, for example the triethylammonium salt, thereof, with a reactive derivative, such as a halide, for example the chloride, of a suitable acid, for example a halogenoformic acid lower alkyl ester, for example chloroformic acid isobutyl ester, or a lower alkanecarboxylic acid halide, for example trichloroacetic acid chloride.

Activated esters of compounds of the formula III, if necessary having a protected amino group, can be prepared, for example, by reacting a corresponding compound having a free carboxyl group, in the presence of a carbodiimide, for example N,N'-dicyclohexylcarbodiimide, with a phenol which is optionally substituted, for example by nitro or halogen, such as chlorine, such as a nitrophenol, for example 4-nitrophenol or 2,4-dinitrophenol, or a polyhalogenophenol, for example 2,3,4,5,6-pentachlorophenol.

The starting materials of the formula IV, which are also active against Gram-positive and Gram-negative microorganisms, such as those mentioned in connection with the compounds of the formula I, and which thus also constitute a subject of the present invention, can be manufactured by introducing the group of the formula

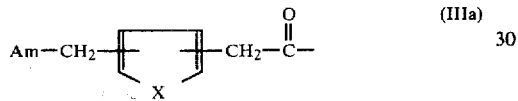

wherein an amino group Am is present, if necessary, in the protected form, into the amino group of a compound of the formula VIII, wherein the amino group can optionally be substituted by a group permitting acylation and wherein the grouping of the formula —S—$A_o$— has the abovementioned meaning, above all by acylation, for example by the acylation process described above for starting materials of the formula II.

The starting materials of the formula IVb can be obtained, for example, when a 6β-amino-penam compound of the formula VIII, or a 7β-amino-3-cephem compound of the formula VIII, wherein functional groups which are present, such as, for example, a carboxyl group of the formula —C(=O)—R, are preferably present in the protected form, is used as the starting material and this is converted, by reaction with an aldehyde, especially an aromatic aldehyde, such as benzaldehyde, into the Schiff's base and this is reacted with an anion-forming agent, such as a preferably sterically hindered alkali metal lower alkanolate, such as potassium tert.-butylate, an alkali metal hydride, for example sodium hydride, an alkali metal-hydrocarbon compound, for example n-butyllithium or phenyllithium, or a suitable alkali metal compound of a secondary organic base, such as, for example, the lithium compound of a di-lower alkylamine or lower alkyleneamine, such as lithium diethylamide, preferably with cooling, for example at temperatures from about −30° C. to about 0° C., and in the presence of a solvent or diluent, such as glycol dimethyl ether. The etherified mercapto group of the formula $R^o$—S— can be introduced into the anion, thus obtainable, direct, for example by treatment with a suitable thiol-sulphonic acid ester, such as a lower alkylthiol-sulphonic acid lower alkyl ester, for example methanethiolsulphonic acid methyl ester, or with a sulphenyl halide, such as a lower alkylsulphenyl halide, for example methylsulphenyl chloride, or indirectly via the corresponding 6α-fluoro-penam Schiff's base or 7α-fluoro-3-cephem Schiff's base; the latter is obtained, for example, by treatment with fluorine perchlorate and it can be converted into the desired 6α-$R^o$-thio-penam Schiff's base or 7α-$R^o$-thio-3-cephem Schiff's base by reaction with a mercaptan, such as a lower alkylmercaptan, for example methylmercaptan, in the presence of a strong acid, such as an optionally halogenated lower alkanecarboxylic acid, for example trifluoroacetic acid. In an intermediate product of this type, the nitrogen atom of the methyleneamino grouping is acylated by introducing the group of the formula IIIa, wherein an amino group Am is present in the protected form if necessary, for example by the process described above and the starting material of the formula IVb is thus obtained. This reaction sequence is carried out, for example, according to the methods described by Slusarchyk et al. J. Org. Chem, Volume 38, page 943 (1973), and Spitzer and Goodson, Tetrahedron Letters, page 273 (1973).

The starting material of the formula V can be obtained, for example, when, in a compound of the formula

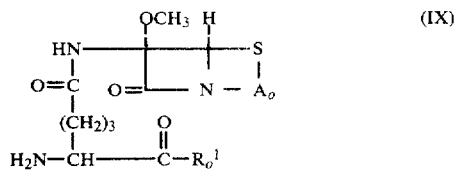

wherein the carboxyl group in a radical in the formula —S—$A_o$— is usually present in the protected form, the amino group in the 5-amino-5-carboxy-valeryl radical is converted into a protected amino group $Am_o$ and the acyl radical of the formula IIIa, wherein an amino group Am is present, if necessary, in a protected form, which differs, in the way it is removed, from that of the protected amino group $Am_o$, is introduced on the nitrogen atom of the amide grouping of a compound which is thus obtainable, for example by acylation according to the process described above, for example by treatment with an acid halide, for example acid chloride, of a compound of the formula III and a suitable silylating agent, such as a mono-silylated or di-silylated acid amide, such as an optionally halogenated N-mono-tri-lower alkylsilyl-lower alkanecarboxylic acid amide or N,N-bis-tri-lower alkylsilyl-lower alkanecarboxylic acid amide, it being possible for the latter also to be present in the N,O-bis-tri-lower alkylsilylated enol form of the amide, for example bis-trimethylsilyl-acetic acid amide or N-trimethylsilyl-trifluoroacetic acid amide, in a suitable solvent or diluent, for example in a halogenated hydrocarbon, such as methylene chloride, and, if necessary, with warming, in a closed vessel and/or in an inert gas atmosphere, such as a nitrogen atmosphere. The manufacture of the starting material of the formula V by the above process can be carried out, for example, according to the method described by Sletzinger et al. J. Am. Chem. Soc., Volume 94, page 1,410 (1972).

The starting material of the formula VI is known or can be prepared in a manner which is in itself known, for example by acylating the amino group in a compound of the formula II by treatment with an acid of the formula

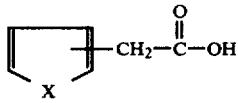

or a suitable derivative, such as a mixed anhydride, especially a halide, for example the chloride, thereof, for example according to the acylation process described above.

2-Cephem starting materials of the formula X can also be prepared analogously to the processes described above in connection with the preparation of the corresponding 3-cephem compounds, for example by acylating the primary amino group in a compound of the formula

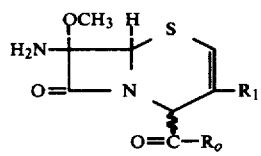

by treatment with an acid of the formula III, wherein an amino group Am is present, if necessary, in the protected form, or with a reactive functional acid derivative thereof or with a salt of such a compound. The above acylation reaction can be carried out, for example, analogously to the methods described above.

In the process according to the invention, and in additional measures which may need to be carried out, as well as in the preparation of the starting materials, it is possible, if necessary, temporarily to protect, in a manner which is in itself known, free functional groups, which do not participate in the reaction, in the starting materials or in the compounds obtainable according to the process, as described above, for example free amino groups by acylation, tritylation or silylation, free hydroxyl or mercapto groups by, for example, etherification or esterification, and free carboxyl groups by, for example, esterification, including silylation, and in each case to liberate them after the reaction has taken place, if desired, in a manner which is in itself known, by solvolysis or reduction.

The pharmacologically usable compounds of the present invention can be used, for example, to manufacture pharmaceutical preparations which contain an effective amount of the active substance together or in a mixture with inorganic or organic, solid or liquid, pharmaceutically usable excipients, which preferably are suitable for parenteral administration.

Preferably, the pharmacologically active compounds of the present invention are used in the form of injectable preparations, for example preparations which can be administered intravenously, or of infusion solutions. Such solutions are preferably isotonic aqueous solutions or suspensions, it being possible to prepare these before use, for example from lyophilised preparations, which contain the active substance along or together with an excipient, for example mannitol. The pharmaceutical preparations can be sterilised and/or contain auxiliaries, for example preservatives, stabilisers, wetting agents and/or emulsifiers, solubilising agents, salts for regulating the osmotic pressure and/or buffers. The present pharmaceutical preparations, which, if desired, can contain further pharmacologically valuable substances, are manufactured in a manner which is in itself known, for example by means of conventional solution or lyophilisation processes and contain from about 0.1% to 100%, especially from about 1% to about 50%, of lyophilisates and up to 100% of the active substance. Depending on the nature of the infection and the condition of the infected organism, daily doses of about 0.5 g to about 5 g are used subcutaneously for the treatment of warm-blooded animals with a weight of about 70 kg.

Unless otherwise defined, the expression "lower" used in connection with the definition of organic radicals or compounds, for example in lower alkyl, lower alkanol and the like, denotes that the particular radicals or compounds contain up to 7, preferably up to 4, carbon atoms.

The examples which follow serve to illustrate the invention.

EXAMPLE 1

2.40 g of 3-acetoxymethyl-7β-[2-(5-tert.-butoxycarbonylaminomethyl-2-thienyl)-acetylamino]-3-cephem-4-carboxylic acid diphenylmethyl ester are dissolved in 180 ml of tetrahydrofurane, the solution is cooled to between −70° and −75° C. under a nitrogen atmosphere and a solution of 0.46 g of lithium methoxide in 10 ml of methanol is added over the course of 1 minute, whilst stirring. After 3 minutes, 0.42 ml of tert.-butyl hypochlorite is added and the solution is stirred for a further 20 minutes at −70° to −75° C., neutralised with 0.80 ml of acetic acid and concentrated to about 70 ml under a waterpump vacuum. 200 ml of water are added and the mixture is extracted with twice 300 ml of ethyl acetate. The organic extracts are washed with water and with a saturated aqueous sodium chloride solution, dried over magnesium sulphate and evaporated under reduced pressure. The crude product is chromatographed on 250 g of silica gel, and 3-acetoxymethyl-7α-methoxy-7β-[2-(5-tert.-butoxycarbonylaminomethyl-2-thienyl)-acetylamino]-3-cephem-4-carboxylic acid diphenylmethyl ester is eluted with a 6:4 mixture of toluene and ethyl acetate; thin layer chromatogram (silica gel): Rf=0.20 (system: toluene/ethyl acetate 6:4); ultraviolet absorption spectrum (in 95% strength aqueous ethanol): $\lambda_{max}=243$ mμ ($\epsilon=13,900$) and $\lambda_{min}=236$ mμ ($\epsilon=13,600$); infrared absorption spectrum (in methylene chloride): characteristic bands at 2.92μ, 5.61μ, 5.74μ, 5.79μ, 6.23μ and 6.67μ.

The starting material can be prepared as follows:

A solution of 20 g of 2-thenylamine hydrochloride in a mixture of 100 ml of trifluoroacetic acid and 100 ml of acetic anhydride is stirred for 2 hours at 55° C., with exclusion of moisture. The reaction mixture is concentrated completely under reduced pressure, 50 ml of toluene are added and the mixture is again concentrated. The crude product is dissolved in ethyl acetate and the solution is treated with active charcoal, filtered through silica gel and concentrated under reduced pressure. After recrystallisation from diethyl ether, 2-acetyl-5-trifluoroacetylaminomethylthiophene is obtained, melting point 83°-84° C.

40 ml of 70% strength aqueous perchloric acid are added to a solution of 34.2 g of thallium-(III) nitrate trihydrate in 100 ml of methanol whilst cooling with ice, and a solution of 20 g of 2-acetyl-5-trifluoroacetylaminothiophene in 500 ml of methanol is added dropwise over the course of 15 minutes at +5° C. under a nitrogen atmosphere. The solution is warmed to 50° C. and stirred at this temperature for 2½ hours. The reaction mixture is cooled to about +5° C. and poured into an ice-cold solution of 120 g of dipotassium hydrogen phosphate in 300 ml of water. The mixture is filtered and the filter residue is washed with methanol. The filtrate is concentrated to about 300 ml under reduced pressure and is extracted with three times 150 ml of chloroform. The extracts are washed with water and subsequently with saturated aqueous sodium chloride solution, dried over magnesium sulphate and concentrated under a waterpump vacuum. This leaves 2-(5-trifluoroacetylaminomethyl-2-thienyl)acetic acid methyl ester; thin layer chromatogram (silica gel: system: toluene/ethyl acetate, 60:40): Rf=0.65; infrared absorption spectrum (in methylene chloride): characteristic bands at 2.93μ, 3.39μ, 5.75μ and 5.80μ.

40 ml of 2 N aqueous sodium hydroxide solution are added to a solution of 9.7 g of 2-(5-trifluoroacetylaminomethyl-2-thienyl)-acetic acid methyl ester in 50 ml of dioxane at 20° C. under a nitrogen atmosphere. The mixture is stirred for 2 hours at 20°-25° C. and diluted with 50 ml of dioxane, and 8.5 ml of tert.-butoxycarbonyl azide are added to the solution, after which it is stirred for a further 16 hours at 20°-25° C. The reaction mixture is cooled to about 5° C. and adjusted to pH 2.5 with about 40 ml of 20% strength aqueous phosphoric acid. It is concentrated to about 50 ml under reduced pressure and extracted with three times 200 ml of ethyl acetate. The extracts are washed with a saturated aqueous sodium chloride solution, dried over magnesium sulphate, decolorised by treatment with an active charcoal preparation and concentrated under reduced pressure. The residue is recrystallised from diethyl ether, and 2-(5-tert.-butoxycarbonylaminomethyl-2-thienyl)-acetic acid, melting point 114°-115° C., is thus obtained.

0.90 g of 2-(5-tert.-butoxycarbonylaminomethyl-2-thienyl)-acetic acid is dissolved in 20 ml of methylene chloride (distilled over phosphorus pentoxide), containing 0.334 g of N-methylmorpholine, the solution, from which moisture is kept excluded, is cooled to −20° C. and 0.45 ml of chloroformic acid isobutyl ester is added dropwise, whilst keeping the temperature at between −15° C. and −20° C. After 30 minutes, a solution of 1.04 g of 3-acetoxymethyl-7β-amino-3-cephem-4-carboxylic acid diphenylmethyl ester in 5 ml of methylene chloride is added, after which stirring is continued for 2 hours at −10° C. and for 8 hours at room temperature. The mixture is poured into ice-cold water, adjusted to pH 8.0 with dipotassium hydrogen phosphate and repeatedly extracted with methylene chloride. The organic extracts are washed with a saturated aqueous sodium chloride solution and dried over magnesium sulphate, after which the solvent is removed under reduced pressure. This gives 3-acetoxymethyl7β-[2-(5-tert.-butoxycarbonylaminomethyl-2-thienyl)-acetylamino]-3-cephem-4-carboxylic acid diphenylmethyl ester as a colourless foam which is directly converted further; thin layer chromatogram (silica gel): Rf=0.71 (system: hexane/ethyl acetate/methanol, 20:40:40). The product can be crystallised from diethyl ether, melting point 134°-136° C.; infrared absorption spectrum (in mineral oil): characteristic bands at 3.03μ, 5.68μ, 5.77μ, 6.02μ, 6.26μ and 6.57μ; ultraviolet absorption spectrum (in 95% strength aqueous ethanol): $\lambda_{max}$=245 mμ ($\epsilon$=15,100).

The starting material can also be obtained as follows:

1.42 g of 2-thienylacetic acid are added in portions to a solution, kept at 0°-5° C., of 1.34 g of N-hydroxymethyl acetamide (Einhorn, Ann. Chem., volume 343, page 264 (1905)) in 10 ml of trifluoroacetic acid, whilst stirring. The mixture is stirred for 2 hours at 0°-5° C. and the trifluoroacetic acid is distilled off under reduced pressure. 30 ml of water are added to the residue and the mixture is extracted with twice 50 ml of ethyl acetate. The organic extracts are washed with a saturated aqueous sodium chloride solution, dried over magnesium sulphate, concentrated under reduced pressure and filtered through silica gel. The residue is crystallised from ethyl acetate and gives 2-(5-acetylaminomethyl-2-thienyl)-acetic acid, thin layer chromatogram (silica gel): Rf=0.61 (system: butanol/acetic acid/water, 45:45:10); infrared absorption spectrum (mineral oil): characteristic bands at 2.95μ, 5.82μ, 6.23μ and 6.38μ.

0.3 ml of a 2 N aqueous sodium hydroxide solution is added to a solution of 0.6 g of 2-(5-acetylaminomethyl-2-thienyl)-acetic acid in 5 ml of dioxane. The mixture is stirred for 12 hours at 55°-60° C. and cooled to 25° C., 0.2 ml of tert.-butoxycarbonyl azide is added, the mixture is stirred for 16 hours at room temperature and 2-(5-tert.-butoxycarbonylaminomethyl-2-thienyl)-acetic acid is isolated in accordance with the process described above.

EXAMPLE 2

A solution of 0.247 g of 3-acetoxymethyl-7β-azide7α-methoxy-3-cephem-4-carboxylic acid diphenylmethyl ester (Cama et al., J. Am. Chem. Soc. volume 94, page 1,408 (1972); German Offenlegungsschrift No. 2,129,675) in 7.6 ml of tetrahydrofurane is hydrogenated in the presence of 0.167 g of platinum oxide and 0.076 g of cobalt-II acetate at room temperature for 1¼ hours with hydrogen under a pressure of 2 atmospheres. The reaction mixture is filtered and the filtrate, containing the 3-acetoxymethyl-7β-amino-7α-methoxy-3-cephem-4-carboxylic acid diphenylmethyl ester is used without further purification in the subsequent acylation step.

A solution of 0.237 g of 2-(5-tert.-butoxycarbonylaminomethyl-2-thienyl)-acetic acid in 20 ml of methylene chloride is treated at −15° C. with 0.095 ml of 4-methylmorpholine, followed by 0.119 ml of chloroformic acid isobutyl ester. The mixture is stirred for 15 minutes at −15° C. and the above solution of the 3-acetoxy-methyl-7β-amino-7α-methoxy-3-cephem-4-carboxylic acid diphenylmethyl ester is then added dropwise at the same temperature. The reaction mixture is stirred at 0° C. for 3 hours, then diluted with methylene chloride and washed with a saturated aqueous solution of sodium bicarbonate and a saturated aqueous solution of sodium chloride. The aqueous wash liquids are extracted with methylene chloride and the combined organic extracts are dried over sodium sulphate, filtered and evaporated under reduced pressure. The residue is subjected to a thick layer chromatogram (silica gel), which is developed with a 5:3 mixture of toluene and ethyl acetate. 3-Acetoxymethyl-7β-[2-(5-tert.-butoxycarbonylaminomethyl-2-thienyl)-acetylamino]-7α-methoxy-3-cephem-4-carboxylic acid diphenylmethyl ester of Rf=0.2 is obtained, and is identical with the product of the process described in Example 1.

EXAMPLE 3

0.168 g of chloromethylene-dimethyl-ammonium chloride (obtained as a solid substance by reaction of equimolar amounts of dimethylformamide and phosgene in methylene chloride) is added to a solution of 0.271 g of 2-(5-tert.-butoxycarbonylaminomethyl-2- thienyl)-acetic acid in 5 ml of methylene chloride at 0° C. and the reaction mixture is stirred for 10 minutes. 0.081 ml of pyridine is then added at 0° C., the mixture is stirred for 5 minutes at this temperature and the solution prepared according to the process of Example 2, containing 3-acetoxymethyl-7β-amino-7α-methoxy-3-cephem-4-carboxylic acid diphenylmethyl ester, is added. The mixture is stirred for 30 minutes at 0° C., then diluted with methylene chloride, and washed with a saturated aqueous solution of sodium bicarbonate and a saturated aqueous solution of sodium chloride. The aqueous wash liquids are extracted with methylene chloride and the combined organic extracts are dried over sodium sulphate, filtered and evaporated under reduced pressure. The residue is subjected to a thick layer chromatogram (silica gel), which is developed with a 5:3 mixture of toluene and ethyl acetate. 3-Acetoxymethyl-7β-[2-(5-tert.-butoxycarbonylaminomethyl-2-thienyl)-acetylamino]-7α-methoxy-3-cephem-4-carboxylic acid diphenylmethyl ester of Rf=0.2 is obtained and is identical with the product of the process described in Example 1.

EXAMPLE 4

A solution of 0.90 g of 3-acetoxymethyl-7α-methoxy-7β-[2-(5-tert.-butoxycarbonylaminomethyl-2-thienyl)-acetylamino]-3-cephem-4-carboxylic acid diphenylmethyl ester in 5 ml of trifluoroacetic acid and 1.5 ml of anisole is left to stand for 30 minutes at 0° C. and evaporated, with addition of 20 ml of toluene, under a waterpump vacuum. The residue is triturated with 10 ml of diethyl ether and 40 ml of petroleum ether and filtered. The filter residue, which contains the trifluoroacetic acid salt of 3-acetoxymethyl-7β-[2-(5-aminomethyl-2-thienyl)-acetylamino]-7α-methoxy-3-cephem-4-carboxylic acid is dried for 5 hours in a high vacuum at room temperature and then dissolved in 30 ml of methanol; the solution is decolorised by adding active charcoal, and filtered. The filtrate is adjusted to pH 6.0 with triethylamine and is then left to stand for 2 hours at 0°-5° C. The inner salt of 3-acetoxymethyl-7β-[2-(5-aminomethyl-2-thienyl)-acetylamino]-7α-methoxy-3-cephem-4-carboxylic acid, which has precipitated, is filtered off and dried for 20 hours under a high vacuum at room temperature; melting point above 180° C. (with decomposition); $[\alpha]_D^{20} = +177° \pm 1°$ (c=0.972 in an 0.15 molar aqueous potassium dihydrogen phosphate/dipotassium hydrogen phosphate buffer solution, pH 7.3–7.4); thin layer chromatogram (silica gel): Rf=0.12 (system: n-butanol/acetic acid/water, 45:45:10); ultraviolet absorption spectrum (in an 0.15 molar aqueous potassium dihydrogen phosphate/dipotassium hydrogen phosphate buffer solution, pH 7.3–7.4): $\lambda_{max}=241$ mμ (ε=15,700) and $\lambda_{min}=214$ mμ (ε=8,700); infrared absorption spectrum (in mineral oil): characteristic bands at 5.66μ, 5.75μ, 6.00μ, 6.34μ and 6.55μ.

EXAMPLE 5

0.028 g of sodium bicarbonate is added to a solution of 0.15 g of the inner salt of 3-acetoxymethyl-7β-[2-(5-aminomethyl-2-thienyl)-acetylamino]-7α-methoxy-3-cephem-4-carboxylic acid and 0.053 g of the sodium salt of 5-mercapto-1-methyl-tetrazole in 7 ml of acetone and 10 ml of water, and the mixture is warmed to 60° C. for 5 hours. It is filtered and the filtrate is concentrated under reduced pressure to a volume of about 10 ml, adjusted to pH 5.5 with acetic acid and left to stand for some hours at 0°-5° C. The precipitate is filtered off and washed with acetone. This gives the inner salt of 7β-[2-(5-aminomethyl-2-thienyl)-acetylamino]-7α-methoxy-3-(1-methyl-5-tetrazolyl-thiomethtyl)-3-cephem-4-carboxylic acid, which is dried for 12 hours under a high vacuum; thin layer chromatogram (silica gel): Rf=0.25 (system: chloroform/methanol, 1:1).

In another variant, the reaction is carried out in the presence of 0.028 g of sodium bicarbonate and 0.055 g of potassium iodide.

EXAMPLE 6

9.1 g of 3-acetoxymethyl-7β-[2-(5-tert.-butoxycarbonylaminomethyl-2-furyl)-acetylamino]-3-cephem-4-carboxylic acid diphenylmethyl ester are dissolved in 400 ml of tetrahydrofurane, the solution is cooled to between −70° and −75° C. under a nitrogen atmosphere and a solution of 1.80 g of lithium methoxide in 50 ml of methanol is added over the course of 1 minute, whilst stirring. After 2 minutes, 1.62 ml of tert.-butyl hypochlorite are added and the mixture is stirred for a further 20 minutes at −70° to −75° C., neutralised with 2.5 ml of acetic acid and concentrated to about 100 ml under a waterpump vacuum. 500 ml of water are added and the mixture is extracted with twice 500 ml of ethyl acetate. The organic extracts are washed with water and with a saturated aqueous sodium chloride solution, dried over magnesium and evaporated under reduced pressure. The crude product is chromatographed on 600 g of silica gel, and 3-acetoxymethyl-7α-methoxy-7β-[2-(5-tert.-butoxycarbonylaminomethyl-2-furyl)-acetylamino]-3-cephem-4-carboxylic acid diphenylmethyl ester is eluted with a 6:4 mixture of toluene and ethyl acetate; thin layer chromatogram (silica gel): Rf=0.30 (system: toluene/ethyl acetate, 6:4); infrared absorption spectrum (in methylene chloride): characteristic bands at 2.92μ, 5.61μ, 5.76μ (broad), 6.24μ and 6.67μ.

The starting material can be prepared as follows:

A mixture of 50 g of furfurylamine and 150 ml of trifluoroacetic anhydride is stirred for 2 hours at room temperature, with exclusion of moisture. 150 ml of acetic acid are added and the mixture is stirred for a further 2 hours at 55° C. The reaction mixture is completely concentrated under reduced pressure, mixed with 50 ml of toluene and again concentrated. The crude product is dissolved in ethyl acetate and the solution is treated with active charcoal, filtered through silica gel and concentrated under reduced pressure. After recrystallisation from diethyl ether, 2-acetyl-5-trifluoroacetaminomethyl-furane, melting point 99°-100° C., is obtained; ultraviolet absorption spectrum (in ethanol): $\lambda_{max}=275$ mμ (ε=15,500).

50 ml of 70% strength perchloric acid are added to a solution of 39.8 g of thallium-(III) nitrate trihydrate in 100 ml of methanol whilst cooling with ice and a solution of 20 g of 2-acetyl-5-trifluoroacetaminomethyl-furane in 500 ml of methanol is added dropwise over the course of 15 minutes at +5° C. under a nitrogen atmosphere. The solution is warmed to 50° C. and stirred at this temperature for 2½ hours. The reaction mixture is cooled to about +5° C. and poured into an ice-cold solution of 120 g of dipotassium hydrogen phosphate in 300 ml of water. The mixture is filtered and the filter residue is washed with methanol. The filtrate is concentrated to about 300 ml under reduced pressure and extracted with three times 150 ml of chloroform. The extracts are washed with water and subsequently with a saturated aqueous sodium chloride solution, dried over magnesium sulphate and concentrated under a waterpump vacuum. This leaves 2-(5-trifluoroacetaminomethyl-2-furyl)-acetic acid methyl ester, thin layer chromatogram (silica gel): Rf=0.35 (system: toluene/ethyl acetate, 60:40); infrared absorption spectrum (in methylene chloride): characteristic bands at 2.49µ, 3.39µ and 5.80µ.

75 ml of a 2 N aqueous sodium hydroxide solution are added to a solution of 18.4 g of 2-(5-trifluoroacetaminomethyl-2-furyl)-acetic acid methyl ester in 100 ml of dioxane at 20° C. under a nitrogen atmosphere. The mixture is stirred for 4 hours at 20°-25° C. and diluted with 100 ml of dioxane, and 34 ml of tert.-butoxycarbonyl azide are added to the solution, after which the mixture is stirred for a further 16 hours at 20°-25° C. The reaction is cooled to about 5° C. and adjusted to pH 2.5 with about 40 ml of 20% strength aqueous phosphoric acid. The mixture is concentrated to a volume of about 100 ml under reduced pressure and is extracted with three times 200 ml of ethyl acetate. The extracts are washed with a saturated aqueous sodium chloride solution, dried over magnesium sulphate, decolorised by treatment with an active charcoal preparation, and concentrated. After recrystallisation from diethyl ether, 2-(5-tert.-butoxycarbonylaminomethyl-2-furyl)-acetic acid, melting point 72°-73° C., is obtained.

1.87 g of 2-(5-tert.-butoxycarbonylaminomethyl-2-furyl)-acetic acid are dissolved in 200 ml of methylene chloride (distilled over phosphorus pentoxide) and 0.80 ml of 4-methylmorpholine, the solution, from which moisture is kept excluded, is cooled to −20° C. and 1.0 ml of chloroformic acid isobutyl ester is added dropwise whilst keeping the temperature at between −15° C. and −20° C. After 30 minutes, a solution of 2.31 g of 3-acetoxymethyl-7β-amino-3-cephem-4-carboxylic acid diphenylmethyl ester is added, after which the mixture is stirred for a further 2 hours at −10° C. and for 8 hours at room temperature. It is then poured out into icecold water, the pH is adjusted to 8.0 with dipotassium hydrogen phosphate and the mixture is repeatedly extracted with methylene chloride. The organic extracts are washed with a saturated aqueous sodium chloride solution and dried over magnesium sulphate, after which the solvent is removed under reduced pressure. 3-Acetoxymethyl-7β-[2-(5-tert.-butoxycarbonylaminomethyl-2-furyl)-acetylamino]-3-cephem-4-carboxylic acid diphenylmethyl ester is obtained as a colourless foam which is directly converted further; thin layer chromatogram (silica gel): Rf=0.84 (system: hexane/ethyl acetate/methanol, 20:40:40).

EXAMPLE 7

A solution of 2.95 g of 3-acetoxymethyl-7α-methoxy-7β-[2-(5-tert.-butoxycarbonylaminomethyl-2-furyl)-acetylamino]-3-cephem-4-carboxylic acid diphenylmethyl ester in 3 ml of anisole and 12 ml of trifluoroacetic acid is left to stand for 30 minutes at 0° C. and is then evaporated, with addition of 100 ml of toluene, under a waterpump vacuum. The residue is triturated with 50 ml of diethyl ether and filtered. The filter residue, which contains the trifluoroacetic acid salt of 3-acetoxymethyl-7β-[2-(5-aminomethyl-2-furyl)-acetylamino]-7α-methoxy-3-cephem-4-carboxylic acid, is dried for 5 hours under a high vacuum at room temperature and then dissolved in 30 ml of methanol; the solution is decolorised by adding active charcoal, and filtered. The filtrate is adjusted to pH 6.0 with triethylamine and then left to stand for 2 hours at 0°-5° C. The inner salt of 3-acetoxymethyl-7β-[2-(5-aminomethyl-2-furyl)-acetylamino]-7α-methoxy-3-cephem-4-carboxylic acid, which has precipitated, is filtered off and dried for 20 hours under a high vacuum at room temperature; melting point above 165° C. (with decomposition); thin layer chromatogram (silica gel): Rf=0.22 (system: chloroform/methanol, 1:1); ultraviolet absorption spectrum (in 95% strength aqueous ethanol): $\lambda_{max}=222$ mµ ($\epsilon=12,500$) and $\lambda_{max2}=266$ mµ ($\epsilon=6,200$); infrared absorption spectrum (in mineral oil): characteristic bands at 5.66µ, 5.77µ, 5.91µ, 6.22µ and 6.52µ.

EXAMPLE 8

4.0 g of 3-acetoxymethyl-7β-[2-(5-tert.-butoxycarbonylaminomethyl-2-thienyl)-acetylamino]-3-cephem-4-carboxylic acid tert.-butyl ester are dissolved in 250 ml of tetrahydrofurane, the solution is cooled to between −70° C. and −75° C. under a nitrogen atmosphere and a lithium methylate solution prepared by dissolving 0.170 g of lithium wire in 30 ml of methanol is added over the course of one minute, whilst stirring. After three minutes, 0.80 ml of tert.-butyl hypochlorite is added and the mixture is stirred for a further 20 minutes at −70° C. to −75° C., neutralised with 4.0 ml of acetic acid and concentrated to a volume of about 70 ml under a waterpump vacuum. 200 ml of water are added and the mixture is extracted with twice 300 ml of ethyl acetate. The organic extracts are washed with water and with a saturated aqueous sodium chloride solution, dried over magnesium and evaporated under reduced pressure. The crude product is reprecipitated from a mixture of ethyl acetate and petroleum ether and the 3-acetoxymethyl-7α-methoxy-7β-[2-(5-tert.-butoxycarbonylaminomethyl-2-thienyl)-acetylamino]-3-cephem-4-carboxylic acid tert.-butyl ester thus obtained is filtered off and dried; thin layer chromatogram (silica gel): Rf=0.48 (system: ethyl acetate/chloroform/acetic acid, 80:19:1); ultraviolet absorption spectrum (in 95% strength aqueous ethanol): $\lambda_{max}=243$ mµ ($\epsilon=15,800$); infrared absorption spectrum (in methylene chloride): characteristic bands at 2.88µ, 2.93µ, 5.61µ, 5.75µ, 5.83µ and 6.66µ.

The starting material can be prepared as follows: 8.15 g of 2-(5-tert.-butoxycarbonylaminomethyl-2-thienyl)-acetic acid are dissolved in 500 ml of methylene chloride containing 3.06 ml of N-methylmorpholine, the solution, from which moisture is kept excluded, is cooled to −20° C. and 4.13 ml of chloroformic acid isobutyl ester are added dropwise whilst keeping the temperature at between −15° C. and −20° C. After 30 minutes, a solution of 9.85 g of 3-acetoxymethyl-7β-amino-3-cephem-4-carboxylic acid tert.-butyl ester in 50 ml of methylene chloride is added, after which the solution is stirred for a further 15 hours whilst slowly raising the temperature to 20° C. to 25° C. The mixture is poured out into ice-cold water, neutralised with dipotassium hydrogen phosphate and extracted repeatedly with methylene chloride. The organic extracts are washed with an aqueous saturated sodium chloride solution and dried over magnesium sulphate, after which the solvent is removed under reduced pressure. The residue is recrystallised from diethyl ether and gives 3-acetoxymethyl-7β-[2-(5-tert.-butoxycarbonylaminomethyl-2-thienyl)-acetylamino]-3-cephem-4-carboxylic acid tert.-butyl ester, melting point 76°-78° C., thin layer chromatogram (silica gel): Rf=0.44 (system: chloroform/ethyl acetate/acetic acid, 80:19:1).

EXAMPLE 9

A solution of 3.80 g of 3-acetoxymethyl-7α-methoxy-7β-[2-(5-tert.-butoxycarbonylaminomethyl-2-thienyl)-acetylamino]-3-cephem-4-carboxylic acid tert.-butyl ester in 15 ml of trifluoroacetic acid is left to stand for 30 minutes and evaporated, with addition of 50 ml of toluene, under a waterpump vacuum. The residue is triturated with 30 ml of diethyl ether and filtered. The filter residue, which contains the trifluoroacetic acid salt of 3-acetoxymethyl-7β-[2-(5-aminomethyl-2-thienyl)-acetylamino]-7α-methoxy-3-cephem-4-carboxylic acid, is converted, as described in Example 4, into the inner salt of 3-acetoxymethyl-7β-[2-(5-aminomethyl-2-thienyl)-acetylamino]-7α-methoxy-3-cephem-4-carboxylic acid.

EXAMPLE 10

1.55 g of 3-acetoxymethyl-7β-[2-(3-tert.-butoxycarbonylaminomethyl-2-thienyl)-acetylamino]-3-cephem-4-carboxylic acid tert.-butyl ester are reacted with 0.065 g of lithium in 20 ml of methanol and 0.31 ml of tert.-butyl hypochlorite in accordance with the method described in Example 8, and 3-acetoxymethyl-7α-methoxy-7β-[2-(3-tert.-butoxycarbonylaminomethyl-2-thienyl)-acetylamino]-3-cephem-4-carboxylic acid tert.-butyl ester is thus obtained; thin layer chromatogram (silica gel): Rf=0.52 (system: toluene/ethyl acetate, 3:2); ultraviolet absorption spectrum (in 95% strength aqueous ethanol): $\lambda_{max}$=241 mμ ($\epsilon$=14,200); infrared absorption spectrum (in methylene chloride): characteteristic bands at 2.88μ, 2.93μ, 5.59μ, 5.74μ, 5.83μ and 6.64μ.

The starting material can be prepared as follows: A mixture of 75.0 g of 3-bromomethyl-thiophene and 78.5 g of potassium phthalimide in 1,000 ml of dimethylformamide is stirred for 90 minutes at 100° C. The reaction mixture is cooled, poured out onto a mixture of ice and water and extracted four times with a total of 1,500 ml of ethyl acetate. The organic extracts are washed with water, dried over magnesium sulphate and concentrated under reduced pressure, whereupon 3-phthaloylaminomethyl-thiophene crystallises out; thin layer chromatogram (silica gel): Rf=0.78 (system: toluene/ethyl acetate, 4:1); ultraviolet absorption spectrum (in 95% strength aqueous ethanol): $\lambda_{max}$=220 mμ ($\epsilon$=44,000); infrared absorption spectrum (in methylene chloride): characteristic bands at 5.59μ, 5.86μ and 6.20μ.

90.8 g of 3-phthaloylaminomethylthiophene are taken up in 250 ml of acetic anhydride, 250 ml of trifluoroacetic acid are added dropwise whilst excluding moisture and the mixture is stirred for 3 hours at 50° C. The reaction solution is then concentrated under reduced pressure, 500 ml of water are added and the mixture is neutralised with a 2 N aqueous sodium hydroxide solution whilst cooling with ice, and is extracted with ethyl acetate. The organic phase is washed with water, dried over magnesium sulphate and concentrated. Mixed crystals consisting of 2-acetyl-3-phthaloylaminomethyl-thiophene and 2-acetyl-4-phthaloylaminomethyl-thiophene are obtained; thin layer chromatogram (silica gel): Rf=0.53 and 0.45 (system: toluene/ethyl acetate, 4:1).

38.0 g of the mixture of 2-acetyl-3-phthaloylaminomethyl-thiophene and 2-acetyl-4-phthaloylaminomethyl-thiophene are dissolved in 1,500 ml of methanol, 65 g of thallium-(III) nitrate trihydrate are added under a nitrogen atmosphere and the mixture is stirred for 6 hours at 50° C. The reaction mixture is cooled to 5°–10° C., neutralised with a 2 N aqueous sodium hydroxide solution, concentrated under reduced pressure and extracted with 1,000 ml of chloroform. The organic extract is washed with a saturated aqueous sodium chloride solution, dried over magnesium sulphate and concentrated. A mixture of 2-(3-phthaloylaminomethyl-2-thienyl)-acetic acid methyl ester and 2-(4-phthaloylaminomethyl-2-thienyl)-acetic acid methyl ester is obtained; thin layer chromatogram (silica gel): Rf=0.59 and 0.54 (system: toluene/ethyl acetate, 4:1).

21 g of the mixture of 2-(3-phthaloylaminomethyl-2-thienyl)-acetic acid methyl ester and 2-(4-phthaloylaminomethyl-2-thienyl)-acetic acid methyl ester are dissolved in 400 ml of dioxane, 50 ml of a 2 N aqueous sodium hydroxide solution are added and the mixture is stirred for 2 hours at 20° C. to 25° C. It is concentrated to a volume of about 200 ml, diluted with 200 ml of water, acidified with 20% strength aqueous phosphoric acid and extracted three times with a total of 400 ml of ethyl acetate. The extracts are dried over magnesium sulphate and evaporated under reduced pressure.

3.0 g of hydrazine hydrate are added to the evaporation residue which has been taken up in 250 ml, and the mixture is warmed to 60° C. for 3½ hours and is then evaporated. The residue is taken up in 200 ml of dioxane and reacted with 75 ml of a 2 N aqueous sodium hydroxide solution and 5.0 ml of tert.-butoxycarbonyl azide. The mixture is stirred for 20 hours at 20° C. to 25° C., concentrated to a volume of about 100 ml, diluted with 100 ml of water and extracted with 200 ml of ethyl acetate. The aqueous solution is adjusted to pH 2 with about 50 ml of 20% strength aqueous phosphoric acid. The precipitate is filtered off, the filter residue is washed with ethyl acetate and the filtrate is extracted with three times 200 ml of ethyl acetate. The organic extracts are washed with a saturated aqueous sodium chloride solution, dried over magnesium sulphate solution and concentrated under reduced pressure. The residue is dried under reduced pressure at 30° C. and a mixture of 2-(3-tert.-butoxycarbonylaminomethyl-2-thienyl)-acetic acid and 2-(4-tert.-butoxycarbonylaminomethyl-2-thienyl)-acetic acid is obtained, which can be separated by chromatography on 200 g of silica gel, using a mixture of chloroform/ethyl acetate/acetic acid (80:19:1) as the migrating agent, thin layer chromatogram: Rf=0.44 and 0.34 respectively (system: chloroform/ethyl acetate/acetic acid, 80:19:1). However, in the next stage the mixture of the two compounds is used.

4.0 g of the mixture of 2-(3-tert.-butoxycarbonylaminomethyl-2-thienyl)-acetic acid and 2-(4-tert.-butoxycarbonylaminomethyl-2-thienyl)-acetic acid are dissolved in 125 ml of methylene chloride, the solution is cooled to −20° C. and 1.80 ml of N-methylmorpholine and 0.864 ml of formic acid isobutyl ester are added whilst excluding moisture. After 30 minutes, a solution of 1.97 g of 3-acetoxymethyl-7β-amino-3-cephem-4-carboxylic acid tert.-butyl ester in 10 ml of methylene chloride is added, after which the reaction is allowed to go to completion over the course of 2 hours at −10° C. and 14 hours at 20° C. The mixture is diluted with water and the organic layer is separated off and washed with a saturated aqueous sodium chloride solution. It is dried over magnesium sulphate and evaporated under reduced pressure. The crude product is chromatographed on 200 g of silica gel. A 4:1 mixture of methylene chloride/ethyl acetate is used to elute first 3-acetoxymethyl-7β-[2-(3-tert.-butoxycarbonylaminomethyl-2-thienyl)-acetylamino]-3-cephem-4-carboxylic acid tert.-butyl ester, thin layer chromatogram (silica gel): Rf=0.55 (system: toluene/ethyl acetate, 6:4); ultraviolet absorption spectrum (in 95% strength aqueous ethanol): $\lambda_{max}=241$ mμ ($\epsilon=14,000$), infrared absorption spectrum (in mineral oil): characteristic bands at 2.97μ, 3.02μ, 5.62μ, 5.72μ, 5.83μ, 5.96μ, 6.05μ, 6.49μ and 6.69μ; proton resonance spectrum (chloroform-d): characteristic signals for the two protons on the thiophene ring: δ=6.94 and 7.17 (AB/J=5.5). Thereafter, the same solvent mixture is used to elute 3-acetoxymethyl-7β-[2-(4-tert.-butoxycarbonylaminomethyl-2-thienyl)-acetylamino]-3-cephem-4-carboxylic acid tert.-butyl ester, thin layer chromatogram (silica gel): Rf=0.41 (system: toluene/ethyl acetate, 6:4); ultraviolet absorption spectrum (in 95% strength aqueous ethanol): $\lambda_{max}=242$ mμ ($\epsilon=14,200$); infrared absorption spectrum (in mineral oil): characteristic bands at 2.99μ, 5.62μ, 5.73μ, 5.83μ and 6.59μ; proton resonance spectrum (chloroform-d): characteristic signals for the two protons on the thiophene ring: δ=6.86(s) and δ=6.99(s).

EXAMPLE 11

A solution of 1.5 g of 3-acetoxymethyl-7α-methoxy-7β-[2-(3-tert.-butoxycarbonylaminomethyl-2-thienyl)-acetylamino]-3-cephem-4-carboxylic acid tert.-butyl ester in 6.0 ml of trifluoroacetic acid is converted in accordance with the process described in Example 4 into the inner salt of 3-acetoxymethyl-7β-[2-(3-aminomethyl-2-thienyl)-acetylamino]-7α-methoxy-3-cephem-4-carboxylic acid, thin layer chromatogram (silica gel): Rf=0.27 (system: n-butanol/acetic acid/water, 45:45:10); ultraviolet absorption spectrum (in water): $\lambda_{max}=237$ mμ ($\epsilon=12,700$); infrared absorption spectrum (in mineral oil): characteristic bands at 5.64μ, 5.57μ, 5.97μ and 6.55μ; proton resonance spectrum (formic acid d₂): characteristic AB-system at δ=7.17 and 7.38 (J=5.5) of the two hydrogen substituents on the disubstituted thiophene ring.

EXAMPLE 12

3-Acetoxymethyl-7α-methoxy-7β-[2-(4-tert.-butoxycarbonylaminomethyl-2-thienyl)-acetylamino]-3-cephem-4-carboxylic acid tert.-butyl ester is prepared in accordance with the process described in Example 10; thin layer chromatogram (silica gel): Rf=0.37 (system: toluene/ethyl acetate, 3:2); ultraviolet absorption spectrum (in 95% strength aqueous ethanol): $\lambda_{max}=243$ mμ ($\epsilon=14,300$); infrared absorption spectrum (in methylene chloride): characteristic bands at 2.89μ; 2.93μ; 5.60μ; 5.75μ; 5.84μ and 6.65μ.

EXAMPLE 13

A solution of 1.5 g of 3-acetoxymethyl-7α-methoxy-7β-[2-(4-tert.-butoxycarbonylaminomethyl-2-thienyl)-acetylamino]-3-cephem-4-carboxylic acid tert.-butyl ester in 6.0 ml of trifluoroacetic acid is converted, analogously to the process described in Example 4, into the inner salt of 3-acetoxymethyl-7β-[2-(4-aminomethyl-2-thienyl)-acetylamino]-7α-methoxy-3-cephem-4-carboxylic acid, thin layer chromatogram (silica gel): Rf=0.27 (system: n-butanol/acetic acid/water, 45:45:10); ultraviolet absorption spectrum (in water), $\lambda_{max}=238$ mμ ($\epsilon=13,100$); infrared absorption spectrum (in mineral oil): characteristic bands at 5.64μ; 5.75μ; 5.98μ and 6.55μ.

EXAMPLE 14

A lithium methoxide solution prepared by dissolving 0.14 g of lithium wire in 20 ml of methanol is added to a solution, first introduced into the vessel under a nitrogen atmosphere, at −70° C., of 4.48 g of 7β-[2-(5-tert.-butoxycarbonylaminomethyl-2-thienyl)-acetylamino]-3-(1-methyl-5-tetrazolylthiomethyl)-3-cephem-4-carboxylic acid diphenylmethyl ester in 100 ml of tetrahydrofuran and 100 ml of methanol. Immediately thereafter, 0.860 ml of tert.-butyl hypochlorite is added, the mixture is stirred for 35 minutes at −70° C. to −75° C., 3.0 ml of acetic acid are added and the mixture is concentrated under reduced pressure. 50 ml of ice-cold water are added to the residue; the aqueous mixture is extracted with twice 100 ml of ethyl acetate. The organic extracts are washed with a saturated aqueous sodium chloride solution, dried over magnesium sulphate, filtered through 10 g of silica gel and concentrated. The residue is triturated with petroleum ether and 7β-[2-(5-tert.-butoxycarbonylaminomethyl-2-thienyl)-acetylamino]-7α-methoxy-3-(1-methyl-5-tetrazolylthiomethyl)-3-cephem-4-carboxylic acid diphenylmethyl ester is filtered off, thin layer chromatogram (silica gel): Rf=0.26 (system: toluene/ethyl acetate, 3:2), ultraviolet absorption spectrum (in 95% strength aqueous ethanol): inflections at 239 mμ ($\epsilon=13,100$) and 276 mμ ($\epsilon=5,800$); infrared absorption spectrum (in mineral oil): characteristic bands at 2.90μ, 5.60μ, 5.78μ and 6.59μ.

The starting material can be obtained, for example, as follows:

2.09 g of p-toluenesulphonic acid monohydrate are added to a suspension of 5.0 g of 7β-amino-3-(1-methyl-5-tetrazolylthiomethyl)-3-cephem-4-carboxylic acid (U.S. Pat. No. 3,516,997) in 200 ml of methanol, whilst stirring; this slowly produces a clear solution, which is concentrated under reduced pressure. Diethyl ether is added and the p-toluenesulphonic acid salt of 7β-amino-3-(1-methyl-5-tetrazolylthiomethyl)-3-cephem-4-carboxylic acid is filtered off. The salt is dissolved in 100 ml of dioxane and 2.5 g of diphenyldiazomethane are added in portions to the solution. The mixture is stirred for 18 hours at room temperature and concentrated under reduced pressure; 100 ml of an 0.1 N aqueous sodium bicarbonate solution are added to the residue and the mixture is extracted with twice 100 ml of ethyl acetate. The organic extracts are washed successively with water and with a saturated aqueous sodium chloride solution, dried over magnesium sulphate and concentrated. The crystallisation from diethyl ether gives 7β-amino-3-(1-methyl-5-tetrazolylthiomethyl)-3-cephem-4-carboxylic acid diphenylmethyl ester, thin layer chromatogram (silica gel): Rf=0.21 (system: chloroform/ethyl acetate/acetic acid, 80:19:1); ultraviolet absorption spectrum (ethanol): $\lambda_{max}=269$ mμ ($\epsilon=6,400$); infrared absorption spectrum (in methylene chloride); characteristic bands at 2.93μ, 5.60μ and 6.15μ.

5.43 g of 2-(5-tert.-butoxycarbonylaminomethyl-2-thienyl)-acetic acid are dissolved in 200 ml of methylene chloride containing 2.20 ml of 4-methyl-morpholine, the solution, from which moisture is kept excluded, is cooled to −20° C. and 2.86 ml of chloroformic acid isobutyl ester are added dropwise. After 30 minutes, a solution of 9.35 g of 7β-amino-3-(1-methyl-5-tetrazolylthiomethyl)-3-cephem-4-carboxylic acid diphenylmethyl ester in 100 ml of methylene chloride is added, after which stirring is continued for one hour at $-20°$ C. and for 16 hours whilst slowly warming to room temperature. The mixture is poured out onto ice-cold water, the organic solution is separated off and the aqueous phase is again extracted with 100 ml of methylene chloride. The organic extracts are washed with saturated aqueous sodium chloride solution, dried over magnesium sulphate and concentrated. Crystallisation of the residue from a mixture of methyl acetate and diethyl ether gives 7β-[2-(5-tert.-butoxycarbonylaminomethyl-2-thienyl)-acetylamino]-3-(1-methyl-5-tetrazolylthiomethyl)-3-cephem-4-carboxylic acid diphenylmethyl ester, thin layer chromatogram (silica gel): Rf=0.38 (system: chloroform/ethyl acetate/acetic acid, 80:19:1); ultraviolet absorption spectrum (in 95% strength aqueous ethanol): shoulders at 242 mμ ($\epsilon$=16,400) and 274 mμ ($\epsilon$=9,200); infrared absorption spectrum (in mineral oil): characteristic bands at 3.03μ, 5.58μ, 5.79μ, 6.12μ and 6.51μ.

The starting material can also be prepared in the following manner:

1.5 ml of triethylamine, 1.6 ml of N,N-dimethylaniline and 2.3 ml of trimethylchlorosilane are added to a suspension of 2.0 g of 7β-amino-3-(1-methyl-5-tetrazolylthiomethyl)-3-cephem-4-carboxylic acid in 60 ml of methylene chloride. The mixture is warmed to 40° C. for 20 minutes, whilst stirring, and is then cooled to $-10°$ C. To this mixture is added a solution of 2-(5-tert.-butoxycarbonylaminomethyl-2-thienyl)-acetic acid chloride in methylene chloride (which is prepared as follows: a solution of 1.95 g of 2-(5-tert.-butoxycarbonylaminomethyl-2-thienyl)-acetic acid in 20 ml of methylene chloride is treated with 0.05 ml of dimethylformamide and 5 ml of oxalyl chloride. The mixture is stirred under a stream of nitrogen for 30 minutes at the reflux temperature, the readily volatile constituents are distilled off under reduced pressure and the oily residue is dissolved in 20 ml of methylene chloride). The reaction mixture is stirred for 2 hours at 0° C. to 25° C. and poured into water, the mixture is adjusted to a pH value of about 7 with sodium bicarbonate, extracted with methylene chloride and acidified cautiously with concentrated hydrochloric acid and the precipitate formed is filtered off. The filter residue is washed with water and dried under reduced pressure at room temperature.

The product, containing 7β-[2-(5-tert.-butoxycarbonylaminomethyl-2-thienyl)-acetylamino]-3-(1-methyl-5-tetrazolylthiomethyl)-3-cephem-4-carboxylic acid, is dissolved in 30 ml of dioxane, 1.5 g of diphenyldiazomethane are added to the solution and the mixture is stirred for 12 hours at room temperature and then concentrated. After crystallisation from a mixture of methyl acetate and diethyl ether, the residue gives 7β-[2-(5-tert.-butoxycarbonylaminomethyl-2-thienyl)-acetylamino]-3-(1-methyl-5-tetrazolylthiomethyl)-3-cephem-4-carboxylic acid diphenylmethyl ester.

EXAMPLE 15

A solution of 3.91 g of 7β-[2-(5-tert.-butoxycarbonylaminomethyl-2-thienyl)-acetylamino]-7α-methoxy-3-(1-methyl-5-tetrazolylthiomethyl)-3-cephem-4-carboxylic acid diphenylmethyl ester in 30 ml of trifluoroacetic acid and 5 ml of anisole is left to stand for one hour at 20° C. with exclusion of moisture and is then concentrated under reduced pressure. The residue is dried for 16 hours under a high vacuum and is then dissolved in 30 ml of methanol. The solution is treated with an active charcoal preparation and filtered. About 0.95 ml of triethylamine is added dropwise to the filtrate until a pH value of 6.0 is reached; the inner salt of 7β-[2-(5-aminomethyl-2-thienyl)-acetylamino]-7α-methoxy-3-(1-methyl-5-tetrazolylthiomethyl)-3-cephem-4-carboxylic acid, which precipitates, is filtered off; thin layer chromatogram (silica gel): Rf=0.10 (system n-butanol/acetic acid/water, 45:45:10); ultraviolet absorption spectrum (in 0.01 N aqueous sodium bicarbonate): $\lambda_{max}$=240 mμ ($\epsilon$=15,900); infrared absorption spectrum (in mineral oil): characteristic bands at 5.67μ, 5.96μ and 6.48μ.

The following compounds are prepared analogously on selecting the corresponding starting materials: 7β-[2-(5-aminomethyl-2-thienyl)-acetylamino]-3,7α-dimethoxy-3-cephem-4-carboxylic acid; 3-aminocarbonyloxymethyl-7β-[2-(5-aminomethyl-2-thienyl)-acetylamino]-7α-methoxy-3-cephem-4-carboxylic acid; 7β-[2-(5-aminomethyl-2-thienyl)-acetylamino]-3-methylaminocarbonyloxymethyl-7α-methoxy-3-cephem-4-carboxylic acid; 7β-[2-(5-aminomethyl-2-thienyl)-acetylamino]-3-N-(2-chloroethyl)-aminocarbonyloxymethyl-7α-methoxy-3-cephem-4-carboxylic acid; and 7β-[2-(5-aminomethyl-2-thienyl)-acetylamino]-7α-methoxy-3-methylthiomethyl-3-cephem-4-carboxylic acid, which are usually obtained in the form of their inner salts.

EXAMPLE 16

A solution of 1.96 g of 7β-[2-(5-tert.-butyloxycarbonylaminomethyl-2-thienyl)-acetylamino]-3-(5-methyl-1,3,4-thiadiazol-2-ylthiomethyl)-3-cephem-4-carboxylic acid tert.-butylester in 150 ml of tetrahydrofuran is treated at $-70°$ with a solution of 0.073 g of lithium in 20 ml of methanol and immediately thereafter with 0.391 ml of tert.-butylhypochlorite. After a reaction time of 15 minutes at $-70°$ 3 ml of acetic acid are added and the reaction mixture is evaporated under about 11 mm Hg. pressure. The residue is taken up in 150 ml of ethyl acetate; the organic solution is washed with a dilute aqueous sodium thiosulfate solution and with a saturated aqueous sodium chloride solution, dried over magnesium sulfate and concentrated to a volume of about 10 ml under about 11 mm Hg. pressure. The concentrated solution is slowly diluted with 100 ml of petroleum ether; the residue is filtered off and dried under high vacuum at room temperature to yield the 7β-[2-(5-tert.-butyloxycarbonylaminomethyl-2-thienyl)acetylamino]-7α-methoxy-3-(5-methyl-1,3,4-thiadiazol-2-ylthiomethyl)-3-cephem-4-carboxylic acid tert.-butyl ester; thin layer chromatography (silicagel): Rf=0.12 (system: toluene/ethyl acetate 3:2).

The starting material is prepared as follows: A solution of 4.08 g of 2-(5-tert.-butyloxycarbonylaminomethyl-2-thienyl)-acetic acid in 200 ml of methylene chloride containing 1.65 ml of 4-methyl-morpholine is cooled to $-20°$ under exclusion of moisture and treated dropwise with 1.95 ml of chloroformic acid isobutyl ester. After 30 minutes a solution of 5.16 g of 7β-amino-3-(5-methyl-1,3,4-thiadiazol-2-ylthiomethyl)-3-cephem-4-carboxylic acid and 7.20 ml N,O-bis-(trimethylsilyl)-acetic acid amide in 150 ml of methylene chloride is added, whereupon the reaction mixture is stirred during one hour at $-20°$ and during four hours while the temperature is allowed to slowly rise to room temperature and is then evaporated under reduced pressure. The residue is dissolved in water with the addition of sodium hydrogen carbonate until the pH reaches 8. The solution is washed with ethyl acetate, the separated aqueous layer is acidified to pH 2 with aqueous phosphoric acid of 20% strength and is extracted with ethyl acetate. The organic extract is washed with a saturated aqueous sodium chloride solution, dried over magnesium sulfate and evaporated under reduced pressure. One thus obtains the 7β-[2-(5-tert.-butyloxycarbonylaminomethyl-2-thienyl)-acetylamino]-3-(5-methyl-1,3,4-thiadiazol-2-ylthiomethyl)-3-cephem-4-carboxylic acid; thin layer chromatogram (silicagel): Rf=0.40 (system: n-butanol-/acetic acid/water 45:45:10), ultraviolet absorption spectrum (ethanol): $\lambda_{max}$ 244 mμ ($\epsilon$=16900); infrared absorption spectrum (in mineral oil): characteristic bonds at 2.93μ, 5.60μ, 5.90μ, and 6.55μ.

A mixture of 6.1 g of dicyclohexylcarbodiimide, 2.1 g of tert.-butanol and 0.06 g a copper(I)-chloride is stirred for five days at room temperature. The resulting suspension of the O-tert.-butyl-N,N-'-dicyclohexyl-isourea is diluted with 30 ml of methylene chloride and added to a solution of 2.0 g of 7β-[2-(5-tert.-butyloxycarbonylaminomethyl-2-thienyl)-acetylamino]-3-(5-methyl-1,3,4-thiadiazol-2-ylthiomethyl)-3-cephem-4-carboxylic acid in 50 ml methylene chloride, kept at room temperature. After five hours the reaction mixture is filtered and the filtrate is evaporated under reduced pressure. The residue is chromatographed using 40 g of silicagel; with ethyl acetate the 7β-[2-(5-tert.-butyloxycarbonylaminomethyl-2-thienyl)-acetylamino]-3-(5-methyl-1,3,4-thiadiazol-2-ylthiomethyl)-3-cephem-4-carboxylic acid tert.-butyl ester is eluted; thin layer chromatogram (silicagel): Rf=0.70 (n-butanol/acetic acid/water 45:45:10).

EXAMPLE 17

A solution of 1.52 g of 7β-[2-(5-tert.-butyloxycarbonylaminomethyl-2-thienyl)-acetylamino]-7α-methoxy-(5-methyl-1,3,4-thiadiazol-2-ylthiomethyl)-3-cephem-4-carboxylic acid tert.-butyl ester in 20 ml of trifluoroacetic acid is allowed to stand for 15 minutes at room temperature and under exclusion of moisture and, after adding toluene, is then evaporated under a pressure of about 11 mm Hg. The residue is triturated with diethyl ether; the resulting trifluoroacetic acid salt of the 7β-[2-(5-aminomethyl-2-thienyl)-acetylamino]-7β-methoxy-3-(5-methyl-1,3,4-thiadiazol-2-ylthiomethyl)-3-cephem-4-carboxylic acid is dried under high vacuum and at room temperature, then dissolved in 20 ml of water. The aqueous solution is washed with ethyl acetate, adjusted to pH 6 by adding triethylamine and concentrated to a volume of about 5 ml under a pressure of about 11 mm Hg. The concentrate is diluted dropwise with 30 ml of acetone; the reaction mixture is allowed to stand for 2 hours at 4° and the precipitate is filtered off. The latter is washed with diethyl ether and dried under high vacuum at room temperature. One thus obtains the inner salt of the 7β-[2-(5-aminomethyl-2-thienyl)-acetylamino]-7α-methoxy-3-(5-methyl-1,3,4-thiadiazol-2-ylthiomethyl)-3-cephem-4-carboxylic acid, thin layer chromatogram (silicagel): Rf=0.11 (system: n-butanol-/acetic acid/water 45:45:10); ultraviolet absorption spectrum (0,1-n. aqueous sodium hydrogen carbonate solution): $\lambda_{max}$=242 mμ ($\epsilon$=16400); infrared absorption spectrum (in mineral oil): characteristic bonds at 5.66μ, 5.97μ, 6.25μ and 6.50μ.

EXAMPLE 18

5.00 g of 3-acetoxymethyl-7β-[2-(5-N-tert.-butoxycarbonyl-N-methyl-aminomethyl-2-thienyl)-acetylamino]-3-cephem-4-carboxylic acid tert.-butyl ester are dissolved in 350 ml of tetrahydrofurane, the solution is cooled to −70 to −75° C. under a nitrogen atmosphere and a solution of lithium methoxide in methanol, which is obtained by dissolving 0.150 g of lithium in 50 ml of methanol, is added in the course of 1 minute, while stirring. After 3 minutes, 0.955 g of tert.-butyl hypochlorite are added and the mixture is stirred for a further 20 minutes at −70° to −75° C., neutralised with 3 ml of acetic acid and concentrated in a water pump vacuum to about 70 ml. 200 ml of water are added and the mixture is extracted with twice 300 ml of ethyl acetate. The organic extracts are washed with water and with a saturated aqueous sodium chloride solution, dried over magnesium sulphate and evaporated under reduced pressure. The crude product is chromatographed on 250 g of silica gel, 3-acetoxymethyl 7α-methoxy-7β-[2-(5-N-tert.-butoxy-carbonyl-N-methylaminomethyl-2-thienyl)acetylamino]-3-cephem-4-carboxylic acid tert.-butyl ester being eluted with a 3:2 mixture of toluene and ethyl acetate; thin layer chromatogram (silica gel): Rf=0.40 (system toluene/ethyl acetate, 3:2).

The starting material can be prepared as follows: 2.3 g of an approximately 55% strength dispersion of sodium hydride in mineral oil are added in portions, under a nitrogen atmosphere at 20°–25° C., to a solution of 5.0 g of 2-(5-tert.-butoxycarbonylaminomethyl-2-thienyl)-acetic acid and 20.9 g of methyl iodide in 100 ml of tetrahydrofurane and 10 ml of dimethylformamide. The mixture is stirred for 7 hours at 20°–25° C., 5 ml of ethanol are added to the reaction solution and the latter is concentrated under reduced pressure. 100 ml of water are added to the residue; the mixture is extracted with ethyl acetate, the pH of the aqueous phase is adjusted to 2 using 20% strength phosphoric acid and the aqueous phase is extracted with twice 100 ml of ethyl acetate.

The two organic extracts are washed with a concentrated aqueous sodium chloride solution, dried over magnesium sulphate and concentrated under reduced pressure. The residue is crystallised from diethyl ether and gives 2-(5-N-tert.-butoxycarbonyl-N-methyl-aminomethyl-2-thienyl)-acetic acid of melting point 100°–101° C.; thin layer chromatogram (silica gel): Rf=0.24 (system: chloroform/ethyl acetate/acetic acid, 80:19:1); ultraviolet absorption spectrum (ethanol): $\lambda_{max}$=242 mμ ($\epsilon$=9,300); infrared absorption spectrum (mineral oil): characteristic bands at 5.77μ and 6.03μ.

1.70 g of 4-methyl-morpholine are added to a solution of 4.80 g of 2-(5-N-tert.-butoxycarbonyl-N-methyl-aminomethyl-2-thienyl)-acetic acid in 250 ml of methylene chloride (distilled over phosphorus pentoxide), the mixture is cooled to −20° C. and 2.30 g of chloroformic acid isobutyl ester are added dropwise. After 30 minutes, a solution of 5.25 g of 3-acetoxy-methyl-7β-amino-3-cephem-4-carboxylic acid tert.-butyl ester in 25 ml of methylene chloride is added, the temperature being maintained at −15° C. to −20° C. The coolant is then removed and the reaction solution is left to stand for 18 hours at room temperature. 100 ml of water are then added, the pH is adjusted to 8.0 with di-potassium hydrogen phosphate and the methylene chloride solution is separated off. The aqueous phase is again extracted with methylene chloride and the two organic phases are washed with a concentrated aqueous sodium chloride solution, dried over magnesium sulphate and concentrated. This gives 3-acetoxymethyl-7β-[2-(5-N-tert.-butoxycarbonyl-N-methyl-aminomethyl-2-thienyl)-acetylamino]-3-cephem-4-carboxylic acid tert.-butyl ester; thin layer chromatogram (silica gel): Rf=0.45 (system: toluene/ethyl acetate, 2:1); ultraviolet absorption spectrum (in 96% strength aqueous ethanol): $\lambda_{max}$=245 mμ ($\epsilon$=14,600); infrared absorption spectrum (in methylene chloride): characteristic bands at 2.93μ, 5.73μ, 5.78μ, 5.90μ and 6.63μ.

EXAMPLE 19

20 ml of trifluoroacetic acid are added to the 3-acetoxymethyl-7β-[2-(5-N-tert.-butoxycarbonyl-N-methyl-aminomethyl-2-thienyl)-acetylamino]-7α-methoxy-3-cephem-4-carboxylic acid tert.-butyl ester, obtained according to the process of Example 1, and the mixture is left to stand for 30 minutes.

The reaction mixture containing the trifluoroacetic acid salt of 3-acetoxymethyl-7α-methoxy-7β-[2-(5-methylaminomethyl-2-thienyl)-acetylamino]-3-cephem-4-carboxylic acid is evaporated under reduced pressure and the residue is taken up in water and rendered neutral by adding triethylamine. This gives the inner salt of 3-acetoxymethyl-7α-methoxy-7β-[2-(5-methylaminomethyl-2-thienyl)-acetylamino]-3-cephem-4-carboxylic acid; thin layer chromatograph (silica gel): Rf=0.28 (system: tert.-butanol/isopropanol/water, 35:35:30); ultraviolet absorption spectrum (in water): $\lambda_{max}$=242 mμ ($\epsilon$=14,800); infrared absorption spectrum (in mineral oil): characteristic bands at 5.67μ, 5.75μ, 6.01μ and 6.55μ.

EXAMPLE 20

A solutin of 0.670 g of 7β-[2-(5-N-tert.-butoxycarbonyl-N-methyl-aminomethyl-2-thienyl)-acetylamino]-3-(1-methyl-5-tetrazolylthiomethyl)-3-cephem-4-carboxylic acid tert.-butyl ester in 50 ml of tetrahydrofurane is treated at −70° C. ith a solution of 0.025 g of lithium in 20 ml of methanol and immediately thereafter with 0.130 ml of tert.-butyl hypochlorite. After a reaction time of 15 minutes at −70° C., 1 ml of acetic acid is added and the reaction mixture is evaporated in a water pump vacuum. The residue is taken up in 50 ml of ethyl acetate; the organic solution is washed with dilute aqueous sodium thiosulphate solution and with saturated aqueous sodium chloride solution, dried over magnesium sulphate and concentrated in a water pump vacuum to a volume of about 5 ml. The concentrated solution is diluted slowly with 40 ml of petroleum ether; the precipitate is filtered off and dried in a high vacuum at room temperature. This gives 7β-[2-(5-N-tert.-butoxycarbonyl-N-methyl-aminomethyl-2-thienyl)-acetylamino]-7α-methoxy-3-(1-methyl-5-tetrazolylthiomethyl)-3-cephem-4-carboxylic acid tert.-butyl ester; thin layer chromatogram (silica gel): Rf=0.21 (system: toluene/ethyl acetate, 3:2).

The starting material can be prepared as follows:

1.54 g of 2-(5-N-tert.-butoxycarbonyl-N-methyl-aminomethyl-2-thienyl)-acetic acid are dissolved in 60 ml of methylene chloride containing 0.60 ml of N-methyl-morpholine, the solution is cooled to −20° C., moisture being excluded, and 0.785 ml of chloroformic acid isobutyl ester are added dropwise. After 30 minutes, a solution prepared from 1.97 g of 7β-amino-3-(1-methyl-5-tetrazolylthiomethyl)-3-cephem-4-carboxylic acid and 2.82 ml of N,O-bis-(trimethylsilyl)-acetamide in 60 ml of methylene chloride is added dropwise, after which the reaction mixture is further stirred for one hour at −20° C. and for 4 hours whilst slowly warming to room temperature and then concentrated under reduced pressure. The residue is dissolved in water, sodium bicarbonate being added until a pH value of 8 is obtained. The solution is washed with ethyl acetate and the aqueous solution, which is separated off, is acidified to pH 2 with 20% strength aqueous phosphoric acid and extracted with ethyl acetate. The organic extract is washed with saturated aqueous sodium chloride solution, dried over magnesium sulphate and concentrated. This gives 7β-[2-(5-N-tert.-butoxycarbonyl-N-methyl-aminomethyl-2-thienyl)-acetylamino]-3-(1-methyl-5-tetrazolylthiomethyl)-3-cephem-4-carboxylic acid; thin layer chromatogram (silica gel): Rf=0.34 (system: n-butanol/acetic acid/water, 75:7.5:21), infrared absorption spectrum (in methylene chloride): characteristic bands at 2.95μ, 5.58μ, 5.84μ and 6.55μ.

A mixture of 2.0 g of dicyclohexylcarbodiimide, 0.86 g of tert.-butyl alcohol and 0.02 g of copper-(I) chloride is stirred for 5 days at room temperature. The suspension of O-tert.-butyl-N,N'-dicyclohexyl-isourea, thus obtainable, is diluted with 10 ml of methylene chloride and added to a solution of 2.5 g of 7β-[2-(5-N-tert.-butoxycarbonyl-N-methylaminomethyl-2-thienyl)-acetylamino]-3-(1-methyl-5-tetrazolylthiomethyl)-3-cephem-4-carboxylic acid in 20 ml of methylene chloride, this solution being kept at room temperature. After 5 hours, the mixture is filtered and the filtrate is concentrated under reduced pressure. The residue is chromatographed on 30 g of silica gel, 7β-[2-(5-N-tert.-butoxycarbonyl-N-methyl-aminomethyl-2-thienyl)-acetylamino]-3-(1-methyl-5-tetrazolylthiomethyl)-3-cephem-4-carboxylic acid tert.-butyl ester being eluted with ethyl acetate; thin layer chromatogram (silica gel): Rf=0.24 (system: toluene/ethyl acetate, 3:2).

EXAMPLE 21

A solution of 0.44 g of 7β-[2-(5-N-tert.-butoxycarbonyl-N-methyl-aminomethyl-2-thienyl)-acetylamino]-7α-methoxy-3-(1-methyl-5-tetrazolylthiomethyl)-3-cephem-4-carboxylic acid tert.-butyl ester in 10 ml of formic acid and 2 ml of trifluoroacetic acid is left to stand for 15 minutes at room temperature, moisture being excluded, and is then evaporated in a water pump vacuum, toluene being added. The residue is triturated with diethyl ether and the trifluoroacetic acid salt of 7β-[2-(5-methylaminomethyl-2-thienyl)-acetylamino]-7α-methoxy-3-(1-methyl-5-tetrazolylthiomethyl)-3-cephem-4-carboxylic acid, thus obtainable, is dried in a high vacuum at room temperature and then dissolved in 20 ml of water. The aqueous solution is washed with ethyl acetate, the pH value is adjusted to 6 with triethylamine and the solution is concentrated under a water pump vacuum to a volume of about 2 ml. This concentrate is diluted by adding 10 ml of acetone dropwise and left to stand for 2 hours at 4° C. and the precipitate is filtered off. The latter is washed with acetone and dried under a high vacuum at room temperature; this gives the inner salt of 7β-[2-(5-methylaminomethyl-2-thienyl)-acetylamino]-7α-methoxy-3-(1-methyl-5-tetrazolylthiomethyl)-3-cephem-4-carboxylic acid; thin layer chromatogram (silica gel): Rf=0.12 (system: n-butanol/acetic acid/water, 45:45:10).

By a suitable selection of the starting materials, the following compounds can be obtained in an analogous manner: 3-acetoxymethyl-7β-[2-(5-dimethylaminomethyl-2-thienyl)-acetylamino]-7α-methoxy-3-cephem-4-carboxylic acid; 7α-methoxy-7β-[2-(5-methylaminomethyl-2-thienyl)-acetylamino]-3-(5-methyl-1,3,4-thiadiazol-2-ylthiomethyl)-3-cephem-4-carboxylic acid; 7β-[2-(5-dimethylaminomethyl-2-thienyl)-acetylamino]-7α-methoxy-3-(5-methyl-1,3,4-thiadiazol-2-ylthiomethyl)-3-cephem-4-carboxylic acid; 7β-[2-(5-dimethylaminomethyl-2-thienyl)-acetylamino]-7α-methoxy-3-(1-methyl-5-tetrazolylthiomethyl)-3-cephem-4-carboxylic acid and 3-carbamoyloxymethyl-7α-methoxy-7β-[2-(5-methylaminomethyl-2-thienyl)-acetylamino]-3-cephem-4-carboxylic acid which are usually obtained in the form of their inner salts.

EXAMPLE 22

Dry ampoules or phials, containing 0.5 g of the inner salt of 3-acetoxymethyl-7α-methoxy-7β-[2-(5-methylaminomethyl-2-thienyl)-acetylamino]-3-cephem-4-carboxylic acid, are manufactured as follows:

| Composition (for 1 ampoule or phial) | |
|---|---|
| inner salt of 3-acetoxymethyl-7α-methoxy-7β-[2-(5-methylaminomethyl-2-thienyl)-acetylamino]-3-cephem-4-carboxylic acid | 0.5 g |
| mannitol | 0.5 g |

A sterile aqueous solution of the inner salt of 3-acetoxymethyl-7α-methoxy-7β-[2-(5-methylaminomethyl-2-thienyl)-acetylamino]-3-cephem-4-carboxylic acid and mannitol is sealed, under aseptic conditions, in 5 ml ampoules or 5 ml phials and checked.

EXAMPLE 23

Dry ampoules of phials, containing 0.5 g of the inner salt of 3-acetoxymethyl-7β-[2-(5-aminomethyl-2-thienyl)acetylamino]-7α-methoxy-3-cephem-4-carboxylic acid, are produced as follows:

| Composition (for 1 ampoule or phial) | |
|---|---|
| 3-Acetoxymethyl-7β-[2-(5-aminomethyl-2-thienyl)-acetylamino]-7α-methoxy-3-cephem-4-carboxylic acid, inner salt | 0.5 g |
| Mannitol | 0.05 g |

A sterile aqueous solution of the inner salt of 3-acetoxymethyl-7β-[2-(5-aminomethyl-2-thienyl)-acetylamino]-7α-methoxy-3-cephem-4-carboxylic acid and of the mannitol is sealed in 5 ml ampoules or 5 ml phials under aseptic conditions, and tested.

EXAMPLE 24

Dry powders or phials, containing 0.5 g of the inner salt of 7β-[2-(5-aminomethyl-2-thienyl)-acetylamino]-7α-methoxy-3-(1-methyl-5-tetrazolyl-thiomethyl)-3-cephem-4-carboxylic acid are prepared as follows:

| Composition (for 1 ampoule or phial) | |
|---|---|
| 7β-[2-(5-Aminomethyl-2-thienyl)-acetylamino]-7α-methoxy-3-(1-methyl-5-tetrazolyl-thiomethyl)-3-cephem-4-carboxylic acid, inner salt | 0.5 g |
| Mannitol | 0.05 g |

A sterile aqueous solution of the inner salt of 7β-[2-(5-aminomethyl-2-thienyl)-acetylamino]-7α-methoxy-3-(1-methyl-5-tetrazolyl-thiomethyl)-3-cephem-4-carboxylic acid and of the mannitol is subjected to freeze drying under aseptic conditions in 5 ml ampoules or 5 ml phials and the ampoules or phials are sealed and tested.

We claim:
1. A compound of the formula

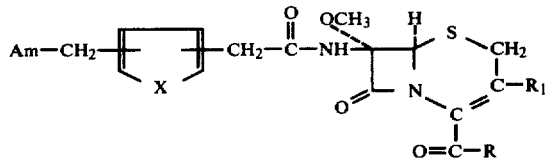

wherein Am represents an unsubstituted amino, lower alkylamino or di-lower alkyl-amino, wherein lower alkyl contains up to 4 carbon atoms, X represents oxygen or sulphur, and the Am-methyl-substituted radical represents Am-methyl-2- or -3-thienyl, or Am-methyl-2-furyl, wherein $R_1$ denotes lower alkoxy or the group of the formula $-CH_2R_2$, in which $R_2$ denotes hydrogen, lower alkanoyloxy, carbamoyloxy, N-lower alkyl or N-halogeno-lower alkylcarbamoyloxy unsubstituted or substituted heterocyclylthio, wherein heterocyclyl represents a monocyclic, five-membered aromatic heterocyclic radical, which is bonded to the thio sulphur atom via a ring carbon atom and which contains 2 or 3 ring nitrogen atoms or additionally a ring oxygen atom, a ring sulphur atom or a ring nitrogen atom, said radical being unsubstituted or substituted by lower alkyl, or wherein heterocyclyl represents an unsaturated monocyclic, six-membered heterocyclic radical, which is bonded to the thio sulphur atom via a ring carbon atom and which contains 2 ring nitrogen atoms, and in which either a ring nitrogen atom carries an oxido group or a ring carbon atom carries an oxo group, said heterocyclyl radical being unsubstituted or substituted by lower alkyl, lower alkoxy or halogen, or $R_2$ denotes a pyridinium radical, which can be substituted by carboxyl, carbamoyl or hydrazinocarbonyl, and wherein R represents hydroxyl, and pharmaceutically acceptable salts thereof.

2. A compound as claimed in claim 1, wherein Am represents unsubstituted amino, methylamino or dimethylamino, X represents sulphur or oxygen and the Am-methyl-substituted radical denotes Am-methyl-2-methyl-2-thienyl or Am-methyl-2-furyl, wherein $R_1$ represents lower alkoxy with up to 4 carbon atoms or represents the radical of the formula $-CH_2-R_2$, in which $R_2$ denotes hydrogen, acetoxy, carbamoyloxy, N-lower alkylcarbamoyloxy, N-halogenolower alkylcarbamoyloxy, thiadiazolylthio or tetrazolylthio which are unsubstituted or substituted by lower alkyl and which are bonded to the thio sulphur atom via a ring carbon atom, N-oxido-pyridazinylthio which is unsubstituted or substituted by lower alkyl, lower alkoxy or halogen and which is bonded to the thio sulphur atom via a ring carbon atom, or pyridinium radical which is unsubstituted or substituted by carbamoyl, and wherein R represents hydroxyl, and pharmaceutically acceptable salts thereof.

3. A compound as claimed in claim 1, wherein Am represents unsubstituted amino, methylamino or dimethylamino, X represents sulphur or oxygen and the Am-methyl-substituted radical denote Am-methyl-2-thienyl or Am-methyl-2-furyl, wherein $R_1$ represents methoxy or the radical of the formula $-CH_2-R_2$, in which $R_2$ denotes hydrogen, acetoxy, carbamoyloxy, methylcarbamoyloxy, ethylcarbamoyloxy, 2-chloroethylcarbamoyloxy, methylthio, 5-methyl-1,3,4-thiadiazol-2-ylthio or 1-methyl-5-tetrazolylthio, and wherein R represents hydroxyl, and pharmaceutically acceptable salts thereof.

4. A compound of the formula

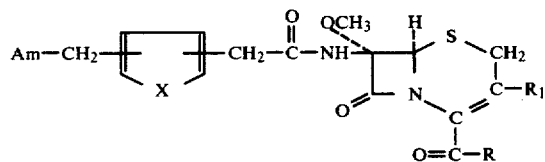

wherein Am represents an amino group of the formula

$R_a$ is hydrogen, $R_b$ represents hydrogen, methyl, or ethyl, X represents sulphur or oxygen, $R_1$ represents methoxy, methylmercapto, lower-alkanoyloxymethyl, carbamoyloxymethyl, thiadiazolylthiomethyl and tetrazolylthiomethyl which are substituted by lower alkyl and which are bonded to the thio sulphur atom via a ring carbon atom, and R represents hydroxyl, and pharmaceutically acceptable salts thereof.

5. A compound as claimed in claim 1 and being 7α-methoxy-7β-[2-(5-ethylaminomethyl-2-thienyl)-acetylamino]-3-(1-methyl-5-tetrazolylthiomethyl)-3-cephem-4-carboxylic acid or a salt thereof.

6. A compound as claimed in claim 1 and being 3-aminocarbonyloxymethyl-7β-[2-(5-aminomethyl-2-thienyl)acetylamino]-7α-methoxy-3-cephem-4-carboxylic acid or a salt thereof.

7. A pharmaceutical preparation comprising an antibiotically effective amount of a compound of claim 1 and a pharmaceutically utilizable excipient.

8. A method for combatting bacterial infection which comprises administering to a warm-blooded animal a preparation of claim 7.

9. A compound as claimed in claim 1 and being a member selected from the group consisting of 3-acetoxymethyl-7β-[2-(5-aminomethyl-2-thienyl)-acetylamino]-7α-methoxy-3-cephem-4-carboxylic acid and a salt thereof.

10. A compound as claimed in claim 1 and being a member selected from the group consisting of 7β-[2-(5-aminomethyl-3-thienyl)-acetylamino]-7α-methoxy-3-(1-methyl-5-tetrazolylthiomethyl)-3-cephem-4-carboxylic acid and a salt thereof.

11. A compound as claimed in claim 1 and being a member selected from the group consisting of 3-acetoxymethyl-7β-[2-(5-aminomethyl-2-furyl)-acetylamino]-7α-methoxy-3-cephem-4-carboxylic acid and a salt thereof.

12. A compound as claimed in claim 1 and being a member selected from the group consisting of 3-acetoxymethyl-7β-[2-(3-aminomethyl-2-thienyl)-acetylamino]-7α-methoxy-3-cephem-4-carboxylic acid and a salt thereof.

13. A compound as claimed in claim 1 and being a member selected from the group consisting of 3-acetoxymethyl-7β-[2-(4-aminomethyl-2-thienyl)-acetylamino]-7α-methoxy-3-cephem-4-carboxylic acid and a salt thereof.

14. A compound as claimed in claim 1 and being a member selected from the group consisting of 7β-[2-(5-aminomethyl-2-thienyl)-acetylamino]-7α-methoxy-3-(5-methyl-1,3,4-thiadiazol-2-ylthiomethyl)-3-cephem-4-carboxylic acid and a salt thereof.

15. A compound as claimed in claim 1 and being a member selected from the group consisting of 3-acetoxymethyl-7α-methoxy-7β-[2-(5-methylaminomethyl-2-thienyl)-acetylamino]-3-cephem-4-carboxylic acid, and a salt thereof.

16. A compound as claimed in claim 1 and being a member selected from the group consisting of 7α-methoxy-7β-[2-(5-methylaminomethyl-2-thienyl)-acetylamino]-3-(1-methyl-5-tetrazolylthiomethyl)-3-cephem-4-carboxylic acid, and a salt thereof.

* * * * *